United States Patent
De Vico et al.

(10) Patent No.: US 6,428,970 B2
(45) Date of Patent: Aug. 6, 2002

(54) CHEMOKINE INHIBITION OF IMMUNODEFICIENCY VIRUS

(75) Inventors: Anthony De Vico, Alexandria, VA (US); Alfredo Garzino-Demo, Baltimore; Robert C. Gallo, Bethesda, both of MD (US)

(73) Assignee: University of Maryland Biotechnology Institute, Baltimore, MD (US)

(*) Notice: Subject to any disclaimer, the term of this patent is extended or adjusted under 35 U.S.C. 154(b) by 0 days.

(21) Appl. No.: 09/747,142

(22) Filed: Dec. 22, 2000

Related U.S. Application Data

(63) Continuation-in-part of application No. 08/826,133, filed on Mar. 26, 1997.

(51) Int. Cl.[7] ............................ G01N 33/53; C12Q 1/70; A61K 45/00; C07K 1/00; C07H 21/04
(52) U.S. Cl. ............................ 435/7.24; 435/5; 435/7.2; 424/85.1; 530/351; 530/395; 536/23.4; 536/23.5
(58) Field of Search ............................ 435/5, 7.2, 7.24; 424/85.1; 530/351, 395; 536/23.4, 23.5

(56) References Cited

U.S. PATENT DOCUMENTS 5,141,867 A  8/1992  Ivanoff et al. ............ 435/252.3

FOREIGN PATENT DOCUMENTS

| WO | WO 90/07119 | 6/1990 |
|----|-------------|--------|
| WO | WO 91/09872 | 7/1991 |
| WO | WO 92/22654 | 12/1992 |
| WO | WO 93/03735 | 3/1993 |

OTHER PUBLICATIONS

Fahey et al., Clin. Exp. Immunol. 88:1–5, 1992.*
Fox, J.L., Bio/Technology 12:128, Feb. 1994.*
Haynes et al., Amn. Med. 28:39–41, 1996.*
Genbank Acc. No. U64197.
SWISS-PROT: P48061.
Alkhatib et al., 1996, "CC CKR5: A RANTES, MIP–1α, MIP–1β receptor as a fusion cofactor for macrophage–tropic HIV–1", *Science* 272: 1955–1958.
Baggiolini et al., 1994, "Interleukin–8 and related chemotactic cytokines–CXC and CC chemokines", *Adv. in Immunol.* 55:97–179.
Barin et al., 1985, "Virus envelope protein of HTLV–III represents major target antigen for antibodies in AIDS patients", *Science* 228: 1094–1096.
Barre–Sinoussi et al., 1983, "Isolation of a T–Lymphotropic retrovirus from a patient at risk for acquired immune deficiency syndrome (AIDS)", *Science* 220:868–870.
Beall et al., 1992, "Conversion of monocyte chemoattractant protein–1 into a neutrophil attractant by substitution of two amino acids", *J. Biol. Chem.* 267:3455–3459.
Bischoff et al., 1993, "RANTES and related chemokines activate human basophil granulocytes through different G protein–coupled receptors", *Eur. J. Immunol.* 23:761–767.
Bazevic et al., 1995, "Helper and cytotoxic T Cell responses of HIV type 1–Infected individuals to synthtic peptides of HIV type 1 rev", *AIDS Res. & Hum Retroviruses* 11:1335–1342.

(List continued on next page.)

Primary Examiner—Hankyel T. Park
(74) Attorney, Agent, or Firm—Marianne Fuierer; Steven J. Hultquist; Yonqzhi Yang

(57) ABSTRACT

The invention relates to therapeutic compositions and methods for treating and preventing infection by an immunodeficiency virus, particularly HIV infection, using chemokine proteins, nucleic acids and/or derivatives or analogs thereof.

34 Claims, 4 Drawing Sheets

Suppression of R5 and X4 HIV infection in PBMC by mixtures of MDC and other HIV-suppressive chemokines

OTHER PUBLICATIONS

Charo et al., 1994, "Molecular cloning and functional expression of two monocyte chemoattractant protein 1 receptors reveals alternative splicing of the carboxyl–terminal tails", *Proc. Natl. Acad. Sci.* USA 91:2752–2756.

Chen–Mayer et al., 1991, "Host range, replicative, and cytopathic properties of human immunodeficiency virus type 1 are determined by very few amino acid changes in tat an gp120", *Virol.* 65:6931–6941.

Choe et al., 1996, "The β–Chemokine receptors CCR3 and CCR5 facilitate infection by primary HIV–1 isolates", *Cell* 85:1135–1148.

Clavel et al., 1986, "Isolation of a new human retrovirus from west african patients with AIDS", *Science* 233:343–346.

Cocchi et al., 1995, "Identification of RANTES, MIP–1α, and MIP–1β as the major HIV–Suppressive factors produced by CD8+ T cells", *Science* 270:1811–1815.

Cocchi et al., 1996, "The V3 domain of the HIV–1 gp120 envelope glycoprotein is critical for chemokine–mediated blockade of infection", *Nature Med.* 2:1244–1247.

Daar et al., 1990, "High concentrations of recombinant soluble CD4 are required to neutralize primary human immunodeficiency virus type 1 isolate", *Proc. Natl. Acad. Sci. USA* 87:6574–6579.

Dalgleish et al., 1984, "The CD4 (T4) antigen is an essential component of the receptor for the AIDS retrovirus", *Nature* 312:763–767.

Daugherty et al., 1996, "Cloning expression, and characterization of the human eosinophil eotaxin receptor", *J. Exp. Med.* 183:2349–2354.

Dang et al., 1996, "Identification of a major co–receptor for primary isolates of HIV–1", *Nature* 381:661–666.

Doranz et al., 1996, "A dual–tropic primary HIV–1 isolate that uses fusin and the β–chemokine receptors CKR–5, CKR–3, and CKR–2b as fusion cofactors", *Cell* 85:1149–1158.

Dragic et al., 1996,"HIV–1 entry into CD4+ cells is mediated by the chemokine receptor CC–CKR–5", *Nature* 381:667–674.

Erickson et al., 1990, "Design, activity, and 2.8 Å crystal structure of a $C_2$ symmetric inhibitor complexed to HIV–1 protease", *Science* 249:527–533.

Feng et al., 1996, "HIV–1 entry cofactor: Functional cDNA cloning of a seven–transmembrane, G protein–coupled receptor", *Science* 272:872–877.

Gallo et al., 1984, "Frequent detection and isolation of cytopathic retroviruses (HTLV–III) from patients with AIDS and at risk for AIDS", *Science* 224:500–503.

Gardner et al., 1981, "The complete nucleotide sequence of an infectious clone of cauliflower mosaic virus by M13mp7 shotgun sequencing", *Nuc. Acids Res.* 9:2871–2888.

Gerard & Gerard, 1994, "The pro–inflammatory seven–transmembrane segment receptors of the leukocyte",, *Curr. Opin. in Immunol.* 6:140–145.

Goff et al., 1981, "Isolation and properties of Moloney murine leukemia virus mutants: Use of a rapid assay for release of virion reverse transcriptase", *J. Virol.* 38:239–248.

Gong et al., 1996, "RANTES and MCP–3 antagonists bind multiple chemokine receptors", *J. Biol. Chem.* 271:10521–10527.

Guyader et al., 1987, "Genome organization and transactivation of the human immonodeficiency virus type 2", *Nature* 326:662–669.

Hammerskjold & Rekosh, 1989, "The molecular biology of the human immunodeficiency virus", *Biochem. Biophys. Acta* 989:269–280.

R. Horuk, 1994, "Molecular properties of the chemokine receptor family", *Trends Pharmacol. Sci.* 15:159–165.

Horuk et al., 1994, "Identification and characterization of a promiscuous chemokine–binding protein in a human erythroleukemic cell line", *J. Biol. Chem.* 269:17730–17733.

Hwang et al., 1991, "Identification of the envelope V3 loop as the primary determinant of cell tropism in HIV–1", *Science* 253:71–74.

Kahn et al., 1990, "The safety and pharmacokinetics of recombinant soluble CD4 (rCD4) in subjects with the acquired immunodeficiency syndrome (AIDS) and AIDS–related complex", *Ann. Int. Med.* 112:254–261.

Kelner et al., 1994, "Lymphotactin: A cytokine that represents a new class of chemokine", *Science* 266:1395–1399.

Kim et al., 1995, "V3–Independent determinants of macrophage tropism in a primary human immunodeficiency virus type 1 isolate", *J. Virol.* 69:1755–1761.

Kitaura et al., 1996, "Molecular cloning of human eotaxin, an eosinophil–selective CC chemokine, and identification of a specific eosinophil eotaxin receptor, cc chemokine receptor 3", *J. Biol. Chem.* 271:7725–7730.

Klatzmann et al., 1984, "T–lymphocyte T4 molecule behaves as the receptor for human retrovirus LAV", *Nature* 312:767–768.

Kunz et al., 1991, "The human leukocyte platelet–activating factor receptor—cDNA cloning, cell surface expression, and construction of a novel epitope–bearing analog", *J. Biol. Chem.* 267:9101–9106.

J.M.A. Lange, 1995, "Triple combinations: Present and future", *J. AIDS Synd. & Hum. Retrovirol.* 10:S77–82.

Liu et al., 1996, "Homozygous defect in HIV–1 coreceptor accounts for resistance of some multiply–exposed individuals to HIV–1 infection", *Cell* 86:367–377.

Loestcher et al., 1996, "Chemokine receptor specific for IP10 and mig: Structure, function, and expression in activated T–lymphocytes", *J. Exp. Med.* 184:963–969.

Maddon et al., 1986, "The T4 gene encodes the AIDS virus receptor and is expressed in the immune system and the brain", *Cell* 47:333–348.

McDougal et al., 1986, "Binding of HTLV–III/LAV to $T4^{30}$ T cells by a complex of the 110K viral protein and the T4 molecule", *Science* 231:382–385.

Miedema et al., 1994, "Changing virus–host interactions in the course of HIV–1 infection", *Immunol. Rev.* 140:35–72.

Miller & Krangel, 1992, "Biology and biochemistry of the chemokines: A family of chemotactic and inflammatory cytokines", *Crit. Rev. in Immunol.* 12:17–46.

Mitsuya et al., 1991, "Targeted therapy of human immunodeficiency virus–related disease", *FASEB J.* 5:2369–2381.

Mitsuya et al., 1990, "Molecular targets for AIDS therapy", *Science* 249:1533–1544.

P.M. Murphy, 1994, "The molecular biology of leukocyte chemoattractant receptors", *Annu. Rev. Immunol.* 12:593–633.

Neote et al., 1993, "Identification of a promiscuous inflammatory peptide receptor on the surface of red blood cells", *J. Biol. Chem.* 268:12247–12249.

Neote et al., 1993, "Molecular cloning, functional expression, and signaling characteristics of a C–C chemokine receptor", *Cell* 72:415–425.

Neote et al., 1994, "Functional and biochemical analysis of the cloned duffy antigen: Identity with the red blood cell chemokine receptor", *Blood* 84:44–52.

O'Brien et al., 1990, "HIV–1 tropism for mononuclear phagocytes can be determined by regions of gp120 outside the CD4–binding domain", *Nature* 348:69–73.

Oravecz et al., 1996, "β–chemokine inhibition of monocytotrophic HIV–1 infection", *J. Immunol.* 157:1329–1332.

Pal et al., 1993, "Conformational perturbation of the envelope glycoprotein gp120 of human immunodeficiency virus type 1 by soluble CD4 and the lectin succinyl Con A", *Virol.* 194:833–837.

Paxton et al., 1996, "Relative resistance to HIV–1 infection of CD4 lymphocytes from persons who remain uninfected despite multiple high–risk sexual exposures", *Nature Med.* 2:412–417.

Perelson et al., 1996, "HIV–1 dynamic in vivo: Virion clearance rate, infected cell life–span, and viral generation time", *Science* 15:1582–1586.

Ponath et al., 1996, "Cloning of the human eosinophil chemoattractant, eotaxin", *J. Clin. Invest.* 97:604–612.

Ponath et al., 1996, "Molecular cloning and characterization of a human eotaxin receptor expressed selectively on eosinophils", *J. Exp. Med.* 183:2437–2438.

Power et al., 1995, "Molecular cloning and functional expression of a novel cc chemokine receptor cDNA from a human basophilic cell line", *J. Biol. Chem.* 270:19495–19500.

Proudfoot et al., 1996, "Extension of recombinant human RANTES by the retention of the initiating methionine produces a potent antagonist", *J. Biol. Chem.* 271:2599–2603.

Rossi et al., 1997, "Identification through bioinformatics of two new macrophage proinflammatory human chemokines", *J. Immunol.* 158:1033–1036.

Samson et al., 1996, "Molecular cloning and functional expression of a new human cc–chemokine receptor gene", *Biochem.* 35:3362–3367.

Sattentau & Moore, 1993, "The role of CD4 in HIV binding and entry", *Philos. Trans. R. Soc. London* (*Biol.*) 342:59–66.

T.J. Schall, 1991, "Biology of the RANTES/SIS cytokine family", *Cytokine* 3:165–183.

Schooley et al., 1990, "Recombinant soluble CD4 therapy in patients with the acquired immunodeficiency syndrome (AIDS) and AIDS–related complex", *Ann. Int. Med.* 112:247–253.

Simon et al., 1991, "Diversity of G proteins in signal transduction", *Science* 252:802–807.

Smith et al., 1987, "Blocking of HIV–1 infectivity by a soluble, secreted form of the CD4 antigen", *Science* 238:1704–1707.

Teich et al., 1984, *RNA Tumor Viruses* Weiss et al. (eds.), CSH–Press, pp. 949–956.

H. Varmus, 1988, "Retroviruses", *Science* 240:1427–1439.

Weiss et al., 1996, "HIV receptors and the pathogenesis of AIDS", *Science* 272:1885–1886.

Willey et al., 1988, "In vitro mutagenesis identifies a region within the envelope gene of the human immunodeficiency virus that is critical for infectivity", *J. Virol.* 62:139–147.

Yarchoan et al., 1989, "Phase 1 study of the administration of recombinant solube CD4 (rCD4) by continuous infusion to patients with AIDS or ARC", *Proc. 5th Int. Conf. on AIDS* MCP 137, p. 564.

Yoshida et al., 1995, "Molecular cloning of a novel C or λ type chemokine, SCM–1", *FEBS Lett.* 360:155–159.

Zhang et al., 1996, "HIV–1 subtype and second–receptor use", *Nature* 383:768.

\* cited by examiner

Total Contribution of Chemokine "X" and MDC to Soluble HIV$_{IIIB}$ Suppressive Activity Produced by Primary CD8+ T Cells $R^2 = 0.8173$
$p = .00005$ I-309 + MDC (total ng/ml)

Percent Reduction in IIIB Suppression by Antibody Combination

Figure 4

CHEMOKINE INHIBITION OF IMMUNODEFICIENCY VIRUS

1. CROSS-REFERENCE TO RELATED APPLICATIONS

This application is a continuation-in-part of U.S. patent application Ser. No. 08/826,133, filed Mar. 26, 1997.

2. FIELD OF THE INVENTION

The present invention relates to therapeutic compositions and methods for treating and preventing infection by an immunodeficiency virus, particularly HIV infection, using chemokine proteins, nucleic acids and/or derivatives or analogs thereof.

3. BACKGROUND OF THE INVENTION

Human immunodeficiency virus (HIV) induces a persistent and progressive infection leading, in the vast majority of cases, to the development of the acquired immunodeficiency syndrome (AIDS) (Barre-Sinoussi et al., 1983, Science 220: 868–870; Gallo et al., 1984, Science 224:500–503). There are at least two distinct types of HIV: HIV-1 (Barre-Sinoussi et al., 1983, Science 220:868–870; Gallo et al., 1984, Science 224:500–503) and HIV-2 (Clavel et al., 1986, Science 233:343–346; Guyader et al., 1987, Nature 326:662–669). In humans, HIV replication occurs predominantly in CD4+ T lymphocyte populations, and HIV infection leads to depletion of this cell type and eventually to immune incompetence, opportunistic infections, neurological dysfunctions, neoplastic growth, and ultimately death.

HIV is a member of the lentivirus family of retroviruses (Teich et al., 1984, RNA Tumor Viruses, Weiss et al., eds., CSH-press, pp. 949–956). Retroviruses are small enveloped viruses that contain a single-stranded RNA genome, and replicate via a DNA intermediate produced by a virally-encoded reverse transcriptase, an RNA-dependent DNA polymerase (Varmus, H., 1988, Science 240:1427–1439). Other retroviruses include, for example, oncogenic viruses such as human T-cell leukemia viruses (HTLV-1,-II,-III), and feline leukemia virus.

The HIV viral particle consists of a viral core, composed in part of capsid proteins designated p24 and p18, together with the viral RNA genome and those enzymes required for early replicative events. Myristylated gag protein forms an outer viral shell around the viral core, which is, in turn, surrounded by a lipid membrane envelope derived from the infected cell membrane. The HIV envelope surface glycoproteins are synthesized as a single 160 kilodalton precursor protein, which is cleaved by a cellular protease during viral budding into two glycoproteins, gp41 and gp120. gp41 is a transmembrane glycoprotein and gp120 is an extracellular glycoprotein which remains non-covalently associated with gp41, possibly in a trimeric or multimeric form (Hammerskjold, M. and Rekosh, D., 1989, Biochem. Biophys. Acta 989:269–280).

HIV, like other enveloped viruses, introduces viral genetic material into the host cell through a viral envelope mediated fusion of viral and target membranes. HIV is targeted to CD4+ cells because a CD4 cell surface protein (CD4) acts as the cellular receptor for the HIV-1 virus (Dalgleish et al., 1984, Nature 312:763–767; Klatzmann et al., 1984, Nature 312:767–768; Maddon et al., 1986, Cell 47:333–348). Viral entry into cells is dependent upon gp120 binding the cellular CD4 receptor molecules (Pal et al., 1993, Virology 194:833–837; McDougal et al., 1986, Science 231:382–385; Maddon et al., 1986, Cell 47:333–348), explaining HIV's tropism for CD4+ cells, while gp41 anchors the envelope glycoprotein complex in the viral membrane. The binding of gp120 to CD4 induces conformational changes in the viral glycoproteins, but this binding alone is insufficient to lead to infection (reviewed by Sattentau and Moore, 1993, Philos. Trans. R. Soc. London (Biol.) 342:59–66).

Studies of HIV-1 isolates have revealed a heterogeneity in their ability to infect different human cell types (reviewed by Miedema et al., 1994, Immunol. Rev. 140:35–72). The majority of extensively passaged laboratory strains of HIV-1 readily infect cultured T cell lines and primary T lymphocytes, but not primary monocytes or macrophages. These strains are termed T-tropic. T-tropic HIV-1 strains are more likely to be found in HIV-1 infected individuals during the late stages of aids (Weiss et al., 1996, Science 272:1885–1886). The majority of primary HIV-1 isolates (i.e., viruses not extensively passaged in culture) replicate efficiently in primary lymphocytes, monocytes and macrophages, but grow poorly in established T cell lines. These isolates have been termed M-tropic. The viral determinant of T- and M-tropism maps to alterations in the third variable region of gp120 (the V3 loop)(Choe et al., 1996, Cell 85:1135–1148; Cheng-Mayer et al., 1991, J. Virol. 65:6931–6941; Hwang et al., 1991, Science 253:71–74; Kim et al., 1995, J. Virol., 69:1755–1761; and O'Brien et al., 1990. Nature 348:69–73). The characterization of HIV isolates with distinct tropisms taken together with the observation that binding to the CD4 cell surface protein alone is insufficient to lead to infection, suggest a requirement for cell-type specific cofactors, in addition to CD4, for HIV-1 entry into the host cell.

Recently, certain chemokines produced by $CD8^+$ T cells have been implicated in suppression of HIV infection. The chemokines RANTES (regulated on activation normal T cell expressed and secreted), macrophage-inflammatory protein-$1\alpha$ and -$1\beta$ (MIP-$1\alpha$ and MIP-$1\beta$, respectively), which are secreted by $CD8^+$ T cells, were shown to suppress HIV-1 p24 antigen production in cells infected with HIV-1 or HIV-2 isolates in vitro (Cocchi et al., 1995, Science 270:1811–1815). Additionally, high levels of these chemokines have been found to be secreted by $CD4^+$ T lymphocytes in individuals that have been exposed to HIV-1 on multiple occasions but, remain uninfected (Paxton et al., 1996, Nature Med. 2:412–417). While RANTES, MIP-$1\alpha$ and MIP-$1\beta$ alone or in combination, potently suppress a variety of primary HIV-1 isolates and macrophage tropic isolates, such as HIV-$1_{BaL}$, some established laboratory strains, such as HIV-$1_{IIIB}$, are refractory to inhibition of infection or replication by these chemokines (Cocchi et al., 1995, Science 270:1811–1815).

Chemokines, or chemoattractant cytokines, are a subgroup of immune factors that mediate chemotactic and other pro-inflammatory phenomena (See, Schall, 1991, Cytokine 3:165–183). Chemokines are small molecules of approximately 70–80 residues in length and can generally be divided into two subgroups, $\alpha$ which have two N-terminal cysteines separated by a single amino acid (CxC) and $\beta$ which have two adjacent cysteines at the N terminus (CC). RANTES, MIP-$1\alpha$ and MIP-$1\beta$ are members of the $\beta$ subgroup (reviewed by Horuk, R., 1994, Trends Pharmacol. Sci, 15:159–165; Murphy, P. M., 1994, Annu. Rev. Immunol., 12:593–633). The amino terminus of the $\beta$ chemokines RANTES, MCP-1, and MCP-3 have been implicated in the mediation of cell migration and inflammation induced by these chemokines. This involvement is suggested by the observation that the deletion of the amino terminal 8 residues of MCP-1, amino terminal 9 residues of MCP-3, and amino terminal 8 residues of RANTES and the addition of a methionine to the amino terminus of RANTES, antagonize the chemotaxis, calcium mobilization and/or enzyme release stimulated by their native counterparts (Gong et al., 1996 J. Biol. Chem. 271:10521–10527; Proudfoot et al., 1996 J. Biol. Chem. 271:2599–2603). Additionally, α chemokine-like chemotactic activity has been introduced into MCP-1 via a double mutation of Tyr 28 and Arg 30 to leucine and valine, respectively, indicating that internal regions of this protein also play a role in regulating chemotactic activity (Beall et al., 1992, J. Biol. Chem. 267:3455–3459).

The monomeric forms of all chemokines characterized thus far share significant structural homology, although the quaternary structures of α and β groups are distinct. While the monomeric structures of the β and α chemokines are very similar, the dimeric structures of the two groups are completely different. An additional chemokine, lymphotactin, which has only one N terminal cysteine has also been identified and may represent an additional subgroup (γ) of chemokines (Yoshida et al., 1995, FEBS Lett. 360:155–159; and Kelner et al., 1994, Science 266:1395–1399).

Receptors for chemokines belong to the large family of G-protein coupled, 7 transmembrane domain receptors (GCR's) (See, reviews by Horuk, R., 1994, Trends Pharmacol. Sci. 15:159–165; and Murphy, P. M., 1994, Annu. Rev. Immunol. 12:593–633). Competition binding and cross-desensitization studies have shown that chemokine receptors exhibit considerable promiscuity in ligand binding. Examples demonstrating the promiscuity among β chemokine receptors include: CC CKR-1, which binds RANTES and MIP-1α(Neote et al., 1993, Cell 72: 415–425), CC CKR-4, which binds RANTES, MIP-1α, and MCP-1 (Power et al., 1995, J. Biol. Chem. 270:19495–19500), and CC CKR-5, which binds RANTES, MIP-1α, and MIP-1β (Alkhatib et al., 1996, Science, in press and Dragic et al., 1996, Nature 381:667–674). Erythrocytes possess a receptor (known as the Duffy antigen) which binds both α and β chemokines (Horuk et al., 1994, J. Biol. Chem. 269:17730–17733; Neote et al., 1994, Blood 84:44–52; and Neote et al., 1993, J. Biol. Chem. 268:12247–12249). Thus the sequence and structural homologies evident among chemokines and their receptors allows some overlap in receptor-ligand interactions.

CC CKR-5 is the major coreceptor for macrophage-tropic strains of HIV-1 (Alkhatib et al., 1996, Science, in press; Choe et al., 1996, Cell 85:1135–1148; Deng et al., 1996, Nature 381:661–666; Doranz et al., 1996, Cell 85:1149–1158; Dragic et al., 1996, Nature 381:667–674). RANTES, MIP-1α, or MIP-1β, the chemokine ligands for this receptor block HIV Env-mediated cell fusion directed by CC CKR-5 (Alkhatib et al., 1996, Science, in press; and Dragic et al., 1996, Nature 381:667–674). Additional support for the role of CC CKR-5 as an M-tropic HIV-1 cofactor comes from the finding that a 32-base pair deletion in the CC CKR-5 gene found in three multiply exposed but uninfected individuals, prevents HIV from infecting macrophages (Liu et al., 1996, Cell 86:367–377). However, only three of the 25 uninfected individuals studied had this mutation.

The V3 loop of gp120 is the major determinant of sensitivity to chemokine inhibition of infection or replication (Cocchi et al., 1996, Nature Medicine 2:1244–1247; and Oravecz et al., 1996, J. lmmunol. 157:1329–1332). Signal transduction through β chemokine receptors is not required for inhibition of HIV infection or replication, since RANTES inhibits HIV-1 infection in the presence of pertussis toxin, an inhibitor of G-protein-mediated signaling pathways (P. M. Murphy 1994, Ann. Rev. Immunol. 12:593–633; Bischoff et al., 1993, Eur. J. Immunol. 23:761–767; and Simon et al., 1991, Science 252:802–807). CxC CKR4, a CxC (α) chemokine receptor, has been shown to be a coreceptor involved in infection by laboratory-adapted HIV-1 strains (Fong et al., 1996, Science 272:872–877). The α chemokine SDF-1, the ligand for this receptor, has been demonstrated to block infection by T-tropic HIV-1 isolates. CxC CKR4 does not bind the beta chemokines RANTES, MIP-1α, or MIP-1β.

Recently, it has been shown that certain primary, syncytium-inducing/T-tropic isolates use both CC CKR5 and CxC CKR4 as coreceptors and are able to switch between the two. Thus, in the presence of RANTES, MIP-1α and MIP-1β, the chemokine ligands for CC CKR5, T-tropic strains are still able to infect cells via the CxC CKR4 coreceptor (Zhang et al., 1996, Nature 383:768).

HIV infection is pandemic and HIV-associated diseases represent a major world health problem. Although considerable effort is being put into the design of effective therapeutics, currently no curative anti-retroviral drugs against AIDS exist. In attempts to develop such drugs, several stages of the HIV life cycle have been considered as targets for therapeutic intervention (Mitsuya et al., 1991, FASEB J. 5:2369–2381). Many viral targets for intervention with the HIV life cycle have been suggested, as the prevailing view is that interference with a host cell protein would have deleterious side effects. For example, virally encoded reverse transcriptase has been one focus of drug development. A number of reverse-transcriptase-targeted drugs, including 2N,3N-dideoxynucleoside analogs such as AZT, ddI, ddc, and d4 T have been developed which have been shown to been active against HIV (Mitsuya et al., 1991, Science 249:1533–1544).

The new treatment regimens for HIV-1 show that a combination of anti-HIV compounds, which target reverse transcriptase (RT), such as azidothymidine (AZT), lamivudine (3TC), dideoxyinosine (ddi), dideoxycytidine (ddc) used in combination with an HIV-1 protease inhibitor have a far greater effect (2 to 3 logs reduction) on viral load compared to AZT alone (about 1 log reduction). For example, impressive results have recently been obtained with a combination of AZT, ddI, 3TC and ritonavir (Perelson et al., 1996, Science 15:1582–1586). However, it is likely that long-term use of combinations of these chemicals will lead to toxicity, especially to the bone marrow. Long-term cytotoxic therapy may also lead to suppression of $CD8^-$ T cells, which are essential to the control of HIV, via killer cell activity (Blazevic et al., 1995, AIDS Res. Hum. Retroviruses 11:1335–1342) and by the release of factors which inhibit HIV infection or replication, notably the chemokines Rantes, MIP-1α and MIP-1β (Cocchi et al., 1995, Science 270:1811–1815). Another major concern in long-term chemical anti-retroviral therapy is the development of HIV mutations with partial or complete resistance (Lange, J. M., 1995, AIDS Res. Hum. Retroviruses 10:S77–82). It is thought that such mutations may be an inevitable consequence of anti-viral therapy. The pattern of disappearance of wild-type virus and appearance of mutant virus due to treatment, combined with coincidental decline in $CD4^+$ T cell numbers strongly suggests that, at least with some compounds, the appearance of viral mutants is a major underlying factor in the failure of AIDS therapy.

Attempts are also being made to develop drugs which can inhibit viral entry into the cell, the earliest stage of HIV infection, by focusing on CD4, the cell surface receptor for HIV. Recombinant soluble CD4, for example, has been shown to inhibit infection of CD4+ T cells by some HIV-1 strains (Smith et al., 1987, Science 238:1704–1707). Certain primary HIV-1 isolates, however, are relatively less sensitive to inhibition by recombinant CD4 (Daar et al., 1990, Proc. Natl. Acad. Sci. USA 87:6574–6579). In addition, recombinant soluble CD4 clinical trials have produced inconclusive results (Schooley et al., 1990, Ann. Int. Med. 112:247–253; Kahn et al., 1990, Ann. Int. Med. 112:254–261; Yarchoan et al., 1989, Proc. Vth Int. Conf. on AIDS, p. 564, MCP 137).

The late stages of HIV replication, which involve crucial virus-specific processing of certain viral encoded proteins, have also been suggested as possible anti-HIV drug targets. Late stage processing is dependent on the activity of a viral protease, and drugs are being developed which inhibit this protease (Erickson, J., 1990, Science 249:527–533). The clinical outcome of these candidate drugs is still in question.

Attention is also being given to the development of vaccines for the treatment of HIV infection. The HIV-1 envelope proteins (gp160, gp120, gp41) have been shown to be the major antigens for anti-HIV antibodies present in AIDS patients (Barin et al., 1985. Science 228:1094–1096). Thus far, therefore, these proteins seem to be the most promising candidates to act as antigens for anti-HIV vaccine development. Several groups have begun to use various portions of gp160, gp120, and/or gp41 as immunogenic targets for the host immune system. See for example, Ivanoff et al., U.S. Pat. No. 5,141,867; Saith et al., WO 92/22654; Shafferman, A., WO 91/09872; Formoso et al., WO 90/07119. To this end, vaccines directed against HIV proteins are problematic in that the virus mutates rapidly rendering many of these vaccines ineffective. Clinical results concerning these candidate vaccines, however, still remain far in the future.

Thus, although a great deal of effort is being directed to the design and testing of anti-retroviral drugs, effective, non-toxic treatments are still needed.

Citation of a reference hereinabove shall not be construed as an admission that such reference is prior art to the present invention.

4. SUMMARY OF THE INVENTION

The present invention relates to prophylactic and therapeutic methods and compositions based on chemokine proteins, nucleic acids, derivatives or analogs thereof that inhibit replication and/or infection of an immunodeficiency virus in vitro or in vivo, decrease viral load, and/or treating or preventing diseases and disorders associated with infection of an immunodeficiency virus. In specific embodiments, the immunodeficiency virus inhibited by the methods and compositions of the invention is HIV.

According to the present invention, different chemokine receptors are involved in immunodeficiency virus infection, depending on the particular isolate. The present invention provides methods of identifying the particular chemokine(s) capable of inhabiting the infection or replication of a viral isolate of a particular patient and of treating such patient. Pharmaceutical compositions comprising chemokines heretofore unknown to be active against HIV are also provided, as well as related methods of treatment or prophylaxis.

The invention also relates to chemokine derivatives or analog(s) that bind to a plurality of chemokine receptors and that are effective at preventing diseases or disorders associated with infection of an immunodeficiency virus, particularly HIV infection. The invention also relates to pharmaceutical compositions containing such therapeutically and prophylactically effective chemokine derivatives or analogs, or the nucleic acids encoding such. In one embodiment, the chemokine derivative or analog binds to one or more β chemokine receptors selected from a group consisting of CC CKR-1, CC CKR-2A, CC CKR-2B, CC CKR-3, CC CKR-4 and CC CKR-5. In a preferred embodiment, the derivative or analog binds to the chemokine receptor CC CKR-5. In another embodiment, the chemokine derivative or analog binds to one or more a chemokine receptors selected from the group consisting of CxC CKR4, IL-8RA, IL-8RB, Mig receptor, γIP-10 receptor, and Duffy antigen. In a preferred embodiment, the derivative or analog binds to both an α chemokine receptor and a β chemokine receptor. In a most preferred embodiment, the derivative or analog binds to both CxC CKR4 and CC CKR-5. In another embodiment, the chemokine derivative or analog binds to 3, 4, 5, 6, 7, 8, 9, 10, 11 or 12 chemokine receptors.

The present invention also relates to pharmaceutical compositions comprising one or more α, β, or γ chemokines, or nucleic acids encoding the foregoing, in an amount effective to inhibit HIV infection or replication. In one embodiment, the pharmaceutical compositions of the invention comprise RANTES, MIP-1α, MIP-1β, MCP-1, MCP-3 or IL-8 nucleic acid encoding RANTES, MIP-1α, MIP-1β, MCP-1, MCP-3 or IL-8 or a therapeutically and prophylactically effective derivative or analog thereof or nucleic acid encoding the same, in combination with another chemokine, nucleic acid encoding another chemokine, or derivative or analog thereof, in an amount effective to treat or prevent diseases or disorders associated with immunodeficiency virus infection, particularly HIV infection, e.g., ARC, AIDS. In another embodiment, the pharmaceutical composition comprises a β chemokine, or nucleic acid encoding a β chemokine, selected from the group consisting of MCP-2, MCP-4, MIP-1γ, MIP-3α, MIP-3β, eotaxin, Exodus, and I-309, MIP-3α, MIP-3β, eotaxin, Exodus, or a therapeutically or prophylactically effective derivative or analog thereof. In an additional embodiment, the pharmaceutical composition comprises an a chemokine, nucleic acid encoding an α chemokine, or therapeutically or prophylactically effective derivative or analog thereof. In a further embodiment, the pharmaceutical composition comprises the γ chemokine lymphotactin, nucleic acid encoding lymphotactin, or a therapeutically or prophylactically effective derivative or analog thereof. In one embodiment, the pharmaceutical composition of the invention comprises an α chemokine, or nucleic acid encoding an α chemokine, selected from the group consisting of γIP-10, PF4, NAP-2, GRO-α, GRO-β, GRO-γ, ENA-78, GCP-2, or a therapeutically effective derivative or analog thereof. In yet another embodiment, the pharmaceutical composition of the invention contains a combination of α, β and/or γ chemokines, nucleic acids encoding α,β and/or γ chemokines, or therapeutically or prophylactically effective derivatives or analogs thereof.

The present invention also relates to therapeutic compositions based on chemokines and nucleic acids encoding chemokines. Therapeutic compounds of the invention include but are not limited to chemokines, nucleic acids encoding chemokines, and derivatives (including fragments and chimerics) and analogs thereof, that are effective at inhibiting replication or infection by an immunodeficiency virus.

The invention further relates to therapeutic methods for treatment and prevention of diseases and disorders associated with infection with an immunodeficiency virus, in particular HIV infection, by administering a therapeutic composition of the invention. More specifically, the invention provides methods for formulating and administering pharmaceutical compositions of the invention that inhibit infection or replication of one or more known isolates of an immunodeficiency virus, preferably of HIV.

The invention further provides methods for inhibiting the infection or replication of an immunodeficiency virus isolate, in particular, an HIV isolate. In a preferred embodiment, the invention provides methods for formulating, on a patient-to-patient basis, a therapeutic composition of the invention for treating diseases and disorders associated with the immunodeficiency virus isolate(s) present in an individual at a given time. Methods for administering the prophylactic or therapeutic compositions of the invention are also provided.

The invention further provides methods for treating or preventing diseases and disorders associated with infections by immunodeficiency viruses, particularly HIV infections, comprising administering a pharmaceutical composition of the invention containing one or more therapeutically and/or prophylactically effective chemokine derivative(s) and/or analog(s) that bind to a plurality of chemokine receptors. Methods for identifying such derivatives or analogs and formulating the prophylactic or therapeutic compositions are also provided.

In a preferred embodiment, the invention relates to a pharmaceutical composition comprising MDC and I-309. In a related aspect, the invention relates to a method for treating HIV infection, the method comprising administering to a subject in need of such treatment a therapeutically effective amount of MDC (and/or analogs. and/or derivatives thereof) and I-309 (and/or analogs and/or derivatives thereof). The MDC (and/or analogs and/or derivatives thereof and I-309 (and/or analogs and/or derivatives thereof) may be administered simultaneously or sequentially. Moreover, the MDC (and/or analogs and/or derivatives thereof) and I-309 (and/or analogs and/or derivatives thereof) are suitably administered together as components of a pharmaceutical composition, along with a pharmaceutically acceptable carrier. The components are preferably administered in a synergistic amount and in a therapeutically effective amount.

5. DEFINITIONS

A "therapeutically effective" amount or dose is an amount or dose which prevents or delays the onset or progression of an indicated disease or other adverse medical condition. The term also includes an amount sufficient to arrest or reduce the severity of an ongoing disease or other adverse medical condition, and also includes an amount necessary to enhance normal physiological functioning.

As used herein, "treatment" of a disease or other adverse medical condition, should be broadly interpreted based on the therapeutic effects described herein as variously including palliative, active, causal, conservative, medical, palliative, prophylactic, and/or symptomatic treatment, treatment designed to delay the onset or progression of the disease or other adverse medical condition, as well as treatment designed to arrest or reducing the severity of an ongoing disease or other adverse medical condition.

As used herein, a "pharmaceutically acceptable" component (such as a salt, carrier, excipient or diluent) of a formulation according to the present invention is a component which (1) is compatible with the other ingredients of the formulation in that it can be combined with the therapeutics of the invention without eliminating the biological activity of the therapeutics; and (2) is suitable for use in non-human animals or humans without undue adverse side effects (e.g., toxicity, irritation, and allergic response). Side effects are "undue" when their risk outweighs the benefit provided by the pharmaceutical composition.

As used herein, a "pharmaceutically acceptable" with reference to the degree of purity of a polypeptide (e.g., a chemokine or chemokine analog or chemokine fragment) or nucleic acid indicates that the polypeptide or nucleic acid (1) is free of contaminating materials that would eliminate the biological activity of the polypeptide or nucleic acid; and (2) is free of contaminating materials that would render the therapeutic (e.g., polypeptide or nucleic acid) unsuitable for administration to humans (for pharmaceutical use) or other animals (for veterinary use) by causing undue adverse side effects (e.g., toxicity, irritation, and allergic response). Side effects are "undue" when their risk outweighs the benefit provided by the therapeutic (e.g., polypeptide or nucleic acid).

The term "substantially pure" when used in reference to a polypeptide or nucleic acid is defined herein to mean a therapeutic (e.g., polypeptide or nucleic acid) that is substantially free from other contaminating proteins, nucleic acids, and other biologicals derived from an original source organism, recombinant DNA expression system, or from a synthetic procedure employed in the synthesis or purification of the therapeutic (e.g., chromatography reagents and polymers, such as acrylamide or agarose). Purity may be assayed by standard methods. Purity evaluation may be made on a mass or molar basis.

6. BRIEF DESCRIPTION OF THE DRAWINGS

FIG. 1 demonstrates how mixtures of chemokines at the low concentrations released by primary activated CD8+ T cells (as determined by ELISA) block both R5 and X4 HIV infection. The figure also shows that even at much higher concentrations, either I-309 or MDC alone have much less antiviral effect, so they must cooperate or synergize to mediate potent antiviral activity in the mix. Also presented for comparison are tests (right panel) with four randomly selected supernatants from activated CD8+ T cells. Two test dilutions are shown. The "50%" sups contain the levels of the chemokines used in the mix.

FIG. 4 shows the same analyses using a mixture of antibodies to I-309 and MDC. This figure shows that the two chemokines contribute very significantly to the natural activity produced by primary CD8+ T cells.

7. DETAILED DESCRIPTION OF THE INVENTION

Figure 1:
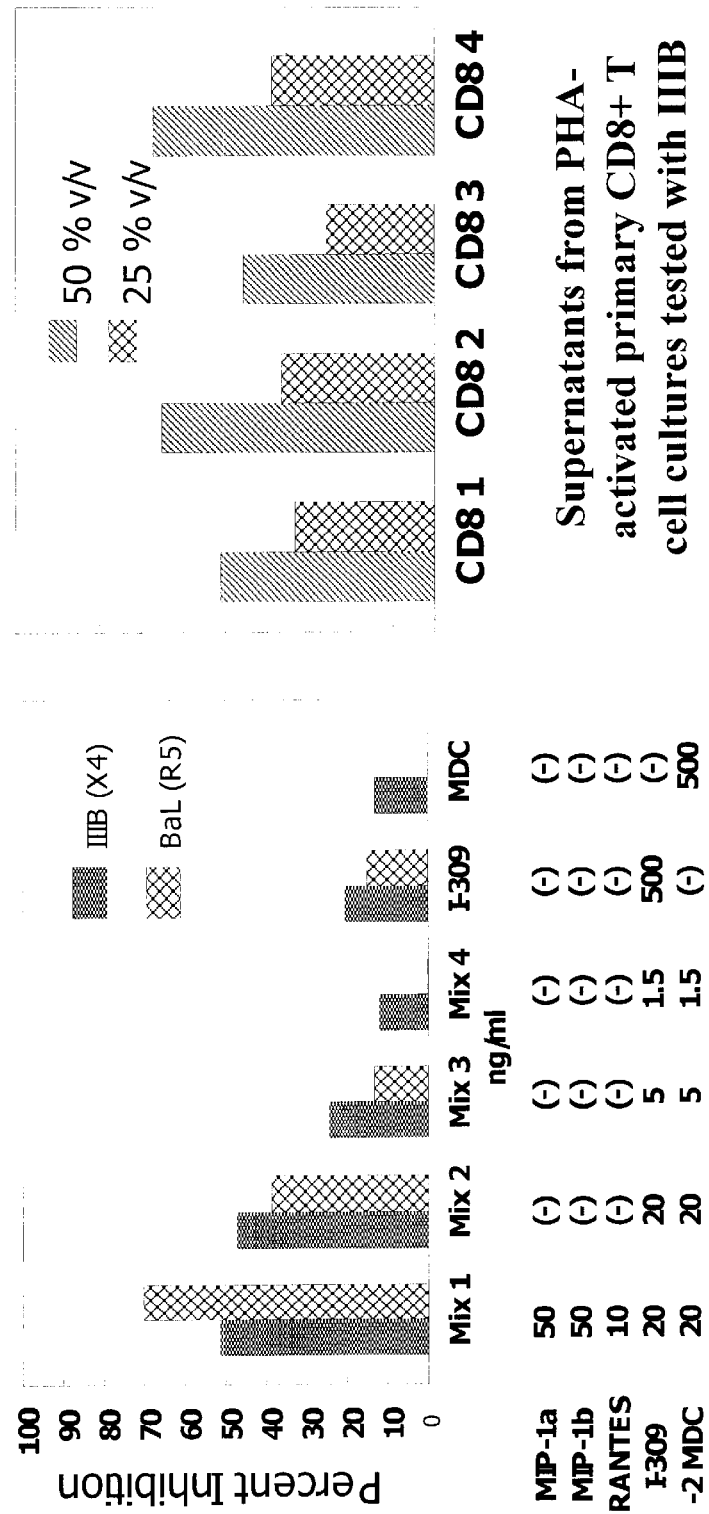

The present invention relates to therapeutic compositions comprising chemokines, nucleic acids encoding chemokines, or derivatives and/or analogs thereof or nucleic acids encoding the same, that are effective at inhibiting replication and/or infection of an immunodeficiency virus in vitro or in vivo, decreasing viral load, and/or treating or preventing diseases and disorders associated with human infection with an immunodeficiency virus. The immunodeficiency virus can be but is not limited to HIV, simian immunodeficiency virus, and feline immunodeficiency virus, and is most preferably HIV.

The invention also relates to therapeutic methods and compositions for the treatment and prevention of diseases and disorders associated with infection by immunodeficiency viruses, preferably HIV infections, by administration of chemokine preparations. The invention provides for treatment of HIV infection by administration of one or more therapeutic compositions of the invention. Therapeutic compounds of the invention include chemokines, nucleic acids encoding chemokines, and related therapeutically and prophylactically effective derivatives and analogs thereof and nucleic acids encoding the same.

Without being bound by any theory, the following theoretical model for HIV transmission is suggested: the HIV-1 envelope initiates infection by binding to the CD4 cell surface protein. This binding induces conformational changes in the envelope protein that increase the exposure of the gp120 V3 loop. The exposed V3 loop then binds to a chemokine receptor, an event that itself triggers further conformational changes leading to fusion and entry of the virus. Depending on their origin (macrophage, $CD4^+$ PBL, T cell line) various isolates of HIV-1 display a requirement for a distinct array of chemokine receptors. The envelope sequence and structure of a given isolate most likely governs which receptor(s) or receptor array is required for entry into the target cell. It is likely that the envelope molecules share a structural homology with chemokines that allows them to interact with various chemokine binding domains.

The Inventors believe that α-chemokines and β-chemokines other than RANTES, MIP-1α and MIP-1β (previously demonstrated by the Inventors to inhibit the infection or replication of HIV-1) will also be able to inhibit the infection or replication of HIV-1, depending upon the GCR requirement of the isolate and the target cell. Accordingly, the invention provides methods for formulating pharmaceutical compositions containing one or more chemokines, nucleic acids encoding chemokines, and/or therapeutically and prophylactically effective derivatives or analogs thereof or nucleic acids encoding the same, that will target and treat diseases and disorders associated with infection by an immunodeficiency virus isolate of interest, particularly a primary HIV isolate. Additionally, the invention provides methods for formulating pharmaceutical compositions which contain (preferably as the only chemokines) the chemokines, nucleic acids encoding chemokines, therapeutically and prophylactically effective derivatives or analogs thereof and/or nucleic acids encoding the same, that treat diseases and disorders associated with isolates of immunodeficiency viruses present in an individual at a given time, by a method comprising testing HIV recovered from the individual for inhibition by one or more, preferably a panel of at least 2, 3, 4, 5, 6, 7, 8, 9, or 10 chemokines, and identifying the chemokine(s), derivative(s), or analog(s) effective at inhibiting HIV infection or replication. Alternatively, the invention provides methods by which to formulate pharmaceutical compositions containing numerous of the chemokines, derivatives and analogs that inhibit the infection or replication of one or more, preferably numerous of the isolates known for a particular immunodeficiency virus, preferably a HIV.

The invention further provides methods by which to formulate pharmaceutical compositions comprising one or more therapeutically and prophylactically effective chemokine derivative(s) or analog(s), or nucleic acids encoding the foregoing, that bind separately to a plurality of α and/or β chemokine receptors. Methods for identifying such derivatives or analogs are also provided.

The invention additionally relates to pharmaceutical compositions comprising one or more α, β, or γ chemokines, or nucleic acid encoding one or more α, β, or γ chemokines, for treatment or prevention of disorders associated with HIV infection. In a specific embodiment, such a composition comprises a therapeutically or prophylactically effective amount of one or more of MCP-1, MCP-2, MCP-3, MCP-4, MIP-1γ, MIP-3α, MIP-3β, eotaxin, Exodus, I-309, γIP-10, PF4, NAP-2, GRO-α, GRO-β, GRO-γ, ENA-78, GCP-2, or lymphotactin. In another embodiment, the pharmaceutical composition further comprises a therapeutically or prophylactically effective amount of a chemokines, chemokine derivatives and/or chemokine analogs thereof, selected from the group consisting of RANTES, MIP-1α, MIP-1β, MCP-1, MCP-3, IL-8, and/or SDF-1. Pharmaceutical compositions comprising nucleic acids encoding such chemokines, derivatives or analogs are also provided.

In another embodiment, the pharmaceutical composition of the invention comprises a therapeutically or prophylactically effective amount of a derivative or analog of one or more α, β, or γ chemokines, or nucleic acid encoding a derivative or analog of one or more α, β, or γ chemokines, for treatment and prevention of disorders associated with HIV infection. In a specific embodiment, such composition comprises a therapeutically or prophylactically effective amount of a derivative or analog of MCP-1, MCP-2, MCP-3, MCP-4, MIP-1γ, MIP-3α, MIP-3β, eotaxin, Exodus, I-309, γIP-10, PF4, NAP-2, GRO-α, GRO-β, GRO-γ, ENA-78, GCP-2, or lymphotactin. In another embodiment, such pharmaceutical composition further comprises a therapeutically or prophylactically effective amount of a chemokines, chemokine derivatives and/or chemokine analogs thereof, selected from the group consisting of RANTES, MIP-1α, MIP-1β, IL-8, and/or SDF-1. Pharmaceutical compositions comprising nucleic acids encoding such chemokines, derivatives or analogs are also provided.

In specific embodiments, the pharmaceutical composition comprises at least 2, 3, 4, 5, 6, 7, 8, 9, or 10 chemokines, derivatives or analogs, or nucleic acids encoding the same. Embodiments wherein the pharmaceutical composition of the invention comprises a plurality of chemokines, derivatives and/or analogs selected from those listed above are further described herein.

The pharmaceutical composition of the invention optionally further comprises a therapeutically or prophylactically effective amount of another anti-HIV agent.

The invention also provides in vitro and in vivo assays for assessing the efficacy of therapeutics of the invention for treatment or prevention of infection with an immunodeficiency virus, in particular HIV infection.

The invention further relates to methods for treating or preventing immunodeficiency virus infection, in particular HIV, in mammals, including humans, by administering the therapeutic compositions of the invention. Methods of administration of the therapeutics of the invention for treatment or prevention of immunodeficiency virus infection are also provided.

The invention also provides methods for inhibiting the infection or replication of any isolate of an immunodeficiency virus, in particular, an HIV isolate. More specifically, the invention provides methods for formulating, on a patient-to-patient basis, a pharmaceutical composition of specific chemokines effective against immunodeficiency virus isolates present in the patient at a given time. Methods for administering a pharmaceutical composition containing chemokines or derivatives or analogs thereof, which inhibit the infection or replication of one or more of all known isolates of a immunodeficiency virus are also provided. In a preferred embodiment the inhibited immunodeficiency virus is HIV.

Additionally, the invention provides methods for treating or preventing immunodeficiency virus infections, by administering an effective amount of a pharmaceutical composition containing chemokine derivatives or analog(s) that bind a plurality of chemokine receptors.

For clarity of disclosure, and not by way of limitation, the detailed description of the invention is divided into the subsections which follow.

7.1 Chemokines, Derivatives and Analogs

The invention provides pharmaceutical compositions comprising chemokines, nucleic acids encoding chemokines, derivatives or analogs thereof, or nucleic acids encoding the derivatives or analogs, that have activity in the treatment and prevention of disorders associated with immunodeficiency virus infection, preferably HIV infection. In a specific embodiment, the compounds of the invention inhibit HIV infection or replication.

In various embodiments, the invention relates to pharmaceutical compositions comprising one or more α, β, or γ chemokines, or nucleic acid encoding one or more α, β, or γ chemokines, for treatment and prevention of disorders associated with HIV infection. In a specific embodiment, such composition comprises a therapeutic or prophylactically effective amount of an α(CxC) chemokine or nucleic acid encoding an α chemokine selected from the group consisting of γ interferon inducible protein-10 (γIP-10), interleukin-8 (IL-8), platelet factor-4 (PF4), neutrophil activating protein (NAP-2), GRO-α, GRO-β, GRO-γ, neutrophil-activating peptide (ENA-78), granulocyte chemoattractant protein-2 (GCP-2), and stromal cell-derived factor-1 (SDF-1, or pre-B cell stimulatory factor (PBSF)); and/or a β(CC) chemokine or nucleic acid encoding a β chemokine selected from the group consisting of: RANTES (regulated on activation, normal T expressed and secreted), macrophage inflammatory protein-1α (MIP-1α). macrophage inflammatory protein-1β (MIP-1β), monocyte chemotactic protein-1(MCP-1), monocyte chemotactic protein-2 (MCP-2), monocyte chemotactic protein-3 (MCP-3), monocyte chemotactic protein-4 (MCP-4) macrophage inflammatory protein-1γ (MIP-1γ), macrophage inflammatory protein-3α (MIP-3α), macrophage inflammatory protein-3β (MIP-3β), eotaxin, Exodus, and I-309; and/or the γ(C) chemokine, or nucleic acid encoding the γ chemokine, lymphotactin. In another embodiment, such compositions comprise a plurality of chemokines, e.g. at least 2, 3, 4, 5, 6, 7, 8, 9, or 10 chemokines, selected from those listed above.

In one embodiment, the pharmaceutical compositions of the invention comprise 1, 2, 3, or 4 chemokines selected from among RANTES, MIP-1α, MIP-1β, or IL-8 or a therapeutically and prophylactically effective derivative or analog thereof, in combination with one or more other chemokines, or a therapeutically and prophylactically effective derivative or analog thereof. Such other chemokines are selected from the group consisting of MCP-1, MCP-2, MCP-3, MCP-4, MIP-1γ, MIP-3α, MIP-3β, eotaxin, Exodus, I-309, γIP-10, PF4, NAP-2, GRO-α, GRO-β, GRO-γ, ENA-78, GCP-2, lymphotactin and SDF-1. Pharmaceutical compositions comprising nucleic acids encoding such chemokines are also provided. In further embodiments, the pharmaceutical composition comprises at least 2, 3, 4, 5, 6, 7, 8, 9, or 10 chemokines, or nucleic acids encoding the same.

In another embodiment, the pharmaceutical composition comprises a β chemokine, or nucleic acid encoding a β chemokine. In specific embodiments, the pharmaceutical composition comprises a β chemokine, or nucleic acid encoding a β chemokine, selected from the group consisting of MCP-2, MCP-4, MIP-1γ, MIP-3α, MIP-3β, eotaxin, Exodus, and I-309, or a therapeutically and prophylactically effective derivative or analog thereof.

In another embodiment, the pharmaceutical composition of the invention comprises an α chemokine, or nucleic acid encoding an α chemokine. In specific embodiments, the pharmaceutical composition comprises an α chemokine, or nucleic acid encoding a α chemokine, selected from the group consisting of γIP-10, PF4, NAP-2, GRO-α, GRO-β, GRO-γ, ENA-78, and GCP-2, and optionally, SDF-1, or a therapeutically or prophylactically effective derivative thereof.

In another embodiment, the pharmaceutical composition comprises an γ chemokine, or nucleic acid encoding a γ chemokine, or a therapeutically or prophylactically effective derivative or analog thereof. In a specific embodiment, the pharmaceutical composition comprises the chemokine lymphotactin, or nucleic acid encoding lymphotactin, or a therapeutically or prophylactically effective derivative or analog thereof.

In a further embodiment, the pharmaceutical composition of the invention comprises a combination of α, β and/or γ chemokines, nucleic acids encoding α, β, or γ chemokines, or therapeutically and prophylactically effective derivatives or analogs thereof. For example, in one embodiment, a pharmaceutical composition comprises αβ chemokine and an α chemokine, in an amount therapeutically or prophylactically effective against disease or disorder associated with HIV infection.

In a specific embodiment, the pharmaceutical composition comprises a therapeutically or prophylactically effective amount (i.e., an amount effective to inhibit immunodeficiency virus replication or infection) of one or more of MCP-1, MCP-2, MCP-3, MCP-4, MIP-1γ, MIP-3α, MIP-3β, eotaxin, Exodus, I-309, γIP-10, PF4, NAP-2, GRO-α, GRO-β, GRO-γ, ENA-78, GCP-2, and lymphotactin. Preferably, the chemokine has been purified. In another embodiment, the pharmaceutical composition further comprises a therapeutically or prophylactically effective amount of one or more chemokines, chemokine derivatives and/or chemokine analogs thereof, selected from the group consisting of RANTES, MIP-1α, MIP-1β, IL-8, and SDF-1. Pharmaceutical compositions comprising nucleic acids encoding such chemokines, derivatives and analogs are also provided.

In another specific embodiment, the pharmaceutical composition comprises a therapeutically or prophylactically effective amount of a derivative or analog of one or more of MCP-1, MCP-2, MCP3, MCP-4, MIP-1γ, MIP-3α, MIP-3β, eotaxin, Exodus, I-309, γIP-10, PF4, NAP-2, GRO-α, GRO-β, GRO-γ, ENA-78, GCP-2, and lymphotactin. Preferably, the chemokine derivative or analog has been purified. In another embodiment, the pharmaceutical composition further comprises a therapeutically or prophylactically effective amount of one or more chemokines, chemokine derivatives and/or chemokine analogs thereof, selected from the group consisting of RANTES, MIP-1α, MIP-1β, IL-8, and SDF-1.

Pharmaceutical compositions comprising nucleic acids encoding such chemokines, derivatives and analogs listed above are also provided.

In another specific embodiment, the pharmaceutical composition comprises a therapeutically or prophylactically effective amount of one or more of MCP-2, MCP-4, MIP-1γ, MIP-3α, MIP-3β, eotaxin, Exodus, I-309, γIP-10, PF4, NAP-2, GRO-α, GRO-β, GRO-γ, ENA-78, GCP-2, and lymphotactin. Preferably, the chemokine has been purified. In another embodiment, such pharmaceutical composition further comprises a therapeutically or prophylactically effective amount of one or more chemokines, chemokine derivatives and/or chemokine analogs selected from the group consisting of RANTES, MIP-1α, MIP-1β, MCP-1, MCP-3, IL-8, and SDF-1. Pharmaceutical compositions comprising nucleic acids encoding such chemokines, derivatives or analogs are also provided.

In another specific embodiment, the pharmaceutical composition comprises a therapeutically or prophylactically effective amount of a derivative or analog of one or more of MCP-2, MCP-4, MIP-1γ, MIP-3α, MIP-3β, eotaxin, Exodus, I-309, γIP-10, PF4, NAP-2, GRO-α, GRO-β, GRO-γ, ENA-78, GCP-2, lymphotactin, and SDF-1. Preferably, the derivative or analog has been purified. In another embodiment, such pharmaceutical composition further comprises a therapeutically or prophylactically effective amount of one or more chemokines, chemokine derivatives and/or chemokine analogs selected from the group consisting of RANTES, MIP-1α, MIP-1β, MCP-1, MCP-3, and IL-8. Pharmaceutical compositions comprising nucleic acids encoding such chemokines, derivatives or analogs are also provided.

In specific embodiments, the pharmaceutical composition comprises at least 2, 3, 4, 5, 6, 7, 8, 9, or 10 chemokines, derivatives (including fragments) or analogs, or nucleic acids encoding the same. In further embodiments, the pharmaceutical composition of the invention comprises only chemokines, derivatives, and/or analogs that have been demonstrated using assays. Examples include those described herein to have activity against a primary HIV isolate.

The pharmaceutical composition of the invention optionally further comprises a therapeutically or prophylactically effective amount of another anti-HIV agent. Examples of other anti-HIV compounds that can be used in such multi-drug regimens include: protease inhibitors (e.g., CRIXIVAN™ (indinavir); FORTOVASE™ and INVIRASE™ (saquinavir); NORVIR™ (ritonavir); and VIRACEPT™ (nelfinavir)); non-nucleoside reverse transcriptase inhibitors (e.g., RESCRIPTOR™ (delavirdine); SUSTIVA™ (efavirenz); and VIRAMUNE™ (nevirapine)); and nucleoside reverse transcriptase inhibitors (e.g., VIDEX™ (didanosine, also known as DDI); EPIVIR™ (lamivudine, also known as 3TC); ZERIT™ (stavudine, also known as d4T); HIVID™ (Zalcitabine, also known as DDC); RETROVIR™ (zidovudine, also known as AZT or ZDV); and COMBIVIR™ (lamivudine and zidovudine)).

In one embodiment, the pharmaceutical composition of the invention comprises a chemokine, or nucleic acid encoding a chemokine, or derivative or analog thereof, that binds to a β chemokine receptor, including, but not limited to, CC CKR-1, CC CKR-2A, CC CKR-2B, CC CKR-3, CC CKR-4 or CC CKR-5. In a preferred embodiment, such chemokines, chemokine derivatives and/or chemokine analogs, binds the chemokine receptor CC CKR-5.

In another embodiment, the pharmaceutical composition comprises a chemokine, or nucleic acid encoding a chemokine, or derivative or analog thereof that binds to an a chemokine receptor, including but not limited to. CxC CKR4, IL-8RA, IL-8RB, Mig receptor, γIP-10 receptor, and Duffy antigen. Preferably, the pharmaceutical composition comprises a chemokine, nucleic acid encoding a chemokine, or derivative or analog thereof that binds separately to an α and β chemokine receptor. In another preferred embodiment, the pharmaceutical composition comprises a chemokines, chemokine derivatives and/or chemokine analogs that binds separately to a plurality of α and/or β chemokine receptors. In a most preferred embodiment, the pharmaceutical composition comprises a chemokine, or a derivative or analog thereof, that binds separately to both CxC CKR4 and CC CKR-5. In further embodiments, the chemokine, derivative and/or analog binds separately to 3, 4, 5, 6, 7, 8, 9, 10, 11, or 12 chemokine receptors. In another preferred embodiment, the derivative or analog of the invention is capable of binding separately to at least 3, 4, 5, 6, 7, 8, 9, 10, 11, or 12 chemokine receptors selected from the group consisting of CC CKR-1, CC CKR-2a, CC CKR-2b, CC CKR-3, CC CKR-4, CC CKR-5, CxC CKR4, IL-8RA, IL-8RB, Mig receptor, γIP-10 receptor, and Duffy antigen. Pharmaceutical compositions containing nucleic acids encoding such chemokines, derivatives and/or analogs are also provided.

In a specific embodiment, the invention relates to RANTES and SDF-1 derivatives and analogs, or nucleic acids encoding RANTES and SDF-1 derivatives and analogs, that comprise, or alternatively consist of an amino acid sequence capable of binding to a chemokine receptor. In a preferred embodiment, the chemokine derivative or analog is a molecule that comprises the amino acid sequence Lys-Asn-Asn-Asn-Arg-Gln-Val (SEQ ID NO:1)(amino acids 45–51 of mature SDF-1 (SWISS-PROT:P48061, Jun. 1, 1996)), which is believed by the Inventors to bind the CxC CKR4 receptor, with the proviso that the molecule is less than 61, 60, 55, 50, 45, 40, 35, 30, 20, 15, 14, 13, 12, 11, 10, 9, 8, or 7 amino acids. In a particular embodiment, the chemokine derivative or analog is a molecule that comprises the amino acid sequence Cys-Ala-Leu-Gln-Ile-Val-Ala-Arg-Leu-Lys-Asn-Asn-Asn-Arg-Gln-Val-Cys (SEQ ID NO:2, amino acids 36–52 of mature SDF-1 (SWISS-PROT:P48061, Jun. 1, 1996)). In a particular embodiment, a fusion protein is provided wherein an SDF-1 sequence is found fused via a peptide bond to a different sequence, and wherein the entire SDF-1 sequence contained in the fusion protein consists of amino acids 45–51 or 36–52 of mature SDF-1, or comprises amino acids 45–51 or 36–52 of mature SDF-1 but has less than 61, 60, 55, 50, 45, 40, 35, 30, 20, 15, 14, 13, 12, 11, 10, 9, 8, or 7 contiguous amino acids of the SDF-1 sequence where applicable, or with conservative substitutions therein. In another embodiment, a peptide is provided whose amino acid sequence consists of amino acids 45–51 or 36–52 of mature SDF-1. In addition, fragments of SDF-1 comprising amino acids 45–51 or 36–52 are provided, as well as such fragments with conservative substitutions. In another preferred embodiment, the chemokine derivative or analog is a molecule that comprises the amino acid sequence Lys-Asn-Arg-Gln-Val (SEQ ID NO:3, amino acids 45–49 of mature RANTES (Schall, 1991, Cytokine 3:165–183)) which is believed by the inventors to bind CC CKR-5, with the proviso that the molecule is less than 58, 55, 50, 45, 40, 35, 30, 20, 15, 14, 13, 12, 11, 10, 9, or 8 amino acids. In a particular embodiment, the chemokines, chemokine derivatives and/or chemokine analogs is a molecule that comprises the amino acid sequence Cys-Ser-Asn-Pro-Ala-Val-Val-Phe-Val-Thr-Arg-Lys-Asn- Arg-Gln-Val-Cys (SEQ ID NO:4, amino acids 34–50 of mature RANTES (Schall, 1991, Cytokine 3:165–183)). In a particular embodiment, a fusion protein is provided wherein an RANTES sequence is found fused via a peptide bond to a different sequence and wherein the entire RANTES sequence contained in the fusion protein consists of amino acids 45–49 or 34–50 of mature RANTES, or comprises amino acids 45–49 or 34–50 of mature RANTES but has less than 58, 55, 50, 45, 40, 35, 30, 20, 15, 14, 13, 12, 11, 10, 9, 8, or 7 contiguous amino acids of the RANTES sequence where applicable, or with conservative substitutions therein. In another embodiment, a peptide is provided whose amino acid sequence consists of amino acids 45–49 or 34–50 of mature RANTES. In addition, fragments of SDF-1 comprising amino acids 45–49 or 34–50 of mature RANTES are provided, as well as such fragments with conservative substitutions. In specific embodiments described infra, RANTES and/or SDF-1 derivatives or analogs comprising the amino acid sequences listed above are joined at amino or carboxy-termini via a peptide bond to an amino acid sequence of a different protein to form a chimeric, or fusion protein.

In a specific embodiment of the invention, proteins consisting of or comprising a fragment of a chemokine consisting of at least 5 (continuous) amino acids of the chemokine is provided. In other embodiments, the fragment consists of at least 6, 7, 8, 9, 10, 15, 20, 30, 40, 50, 60, 70 or 80 amino acids of the chemokine. In specific embodiments, such fragments are not larger than 10, 20, 30, 40, 50, 60, 70 or 80 amino acids. Derivatives or analogs of a chemokine include but are not limited to those molecules exhibiting antiviral activity and that comprise regions that are substantially homologous to a chemokine or fragment thereof (e.g., in various embodiments, at least 60% or 70% or 80% or 90% or 95% identity over an amino acid sequence of identical size or when compared to an aligned sequence wherein the alignment is done by a computer homology program known in the art) or whose encoding nucleic acid is capable of hybridizing to a coding chemokine sequence, under high stringency, moderately high stringency, or low stringency conditions. In a specific embodiment, the chemokine derivative retains the antigenicity (ability to bind to an anti-chemokine antibody) or immunogenicity of the chemokine. Fragments and other derivatives of a chemokine that retain the ability to bind to a chemokine receptor are preferred.

By way of example and not limitation, procedures using conditions of low stringency are as follows (see also Shilo and Weinberg, 1981, Proc. Natl. Acad. Sci. USA 78:6789–6792): Filters containing DNA are pretreated for 6 h at 40EC in a solution containing 35% formamide, 5×SSC, 50 mM tris-HCl (pH 7.5), 5 mM EDTA, 0.1% PVP. 0.1% Ficoll, 1% BSA, and 500 µg/ml denatured salmon sperm DNA. Hybridizations are carried out in the same solution with the following modifications: 0.02% PVP, 0.02% Ficoll, 0.2% BSA, 100 µg/ml salmon sperm DNA, 10% (wt/vol) dextran sulfate, and 5–20×10$^6$ cpm $^{32}$P-labeled probe is used. Filters are incubated in hybridization mixture for 18–20 h at 40EC, and then washed for 1.5 h at 55EC in a solution containing 2×SSC, 25 mM tris-HCl (pH 7.4). 5 mM EDTA, and 0.1% SDS. The wash solution is replaced with fresh solution and incubated an additional 1.5 h at 60EC. Filters are blotted dry and exposed for autoradiography. If necessary, filters are washed for a third time at 65–68EC and reexposed to film. Other conditions of low stringency which may be used are well known in the art.

By way of example and not limitation, procedures using conditions of high stringency are as follows: prehybridization of filters containing DNA is carried out for 8 h to overnight at 65EC in buffer composed of 6×SSC, 50 mM tris-HCl (pH 7.5), 1 mM EDTA, 0.02% PVP, 0.02% Ficoll, 0.02% BSA, and 500 µg/ml denatured salmon sperm DNA. Filters are hybridized for 48 h at 65EC in prehybridization mixture containing 100 µg/ml denatured salmon sperm DNA and 5–20×10$^6$ cpm of $^{32}$P-labeled probe. Washing of filters is done at 37EC for 1 h in a solution containing 2×SSC, 0.01% PVP, 0.01% Ficoll. and 0.01% BSA. This is followed by a wash in 0.1×SSC at 50EC for 45 min before autoradiography. Other conditions of high stringency which may be used are well known in the art.

By way of example and not limitation, procedures using conditions of moderately high stringency are as follows: filters containing DNA are pretreated for 6 hours to overnight at 55EC in buffer composed of 6×SSC, 5×Denhart's 0.5% SDS, 100 mg/mL salmon sperm DNA. Hybridizations are carried out in the same solution upon adding 5–20×10$^6$ cpm of $^{32}$P-labeled probe and incubated 8–48 hours at 55EC. Washing of filters is done at 60EC in 1×SSC, 0.1% SDS, with two exchanges after 30 minutes. Other conditions for moderately high stringency screening are known in the art. For further guidance regarding hybridization conditions see, for example, Sambrook et al., 1989, Molecular Cloning, A Laboratory Manual, Cold Springs Harbor Press, N.Y.; and Ausubel et al., 1989, Current Protocols in Molecular Biology, Green Publishing Associates and Wiley Interscience, N.Y.

The invention also relates to chemokine derivatives or analogs made by altering the chemokine sequence by substitutions, additions or deletions that provide for molecules with anti-viral activity (e.g., inhibit infection or replication of an immunodeficiency virus, preferably HIV) or demonstrate the ability to bind to a chemokine receptor. Thus, the chemokine derivatives include polypeptides containing, as a primary amino acid sequence, all or part of the chemokine amino acid sequence including altered sequences wherein functionally equivalent amino acid residues are substituted for residues within the sequence resulting in a polypeptide which is functionally active. For example, one or more amino acid residues within the sequence can be substituted by another amino acid of a similar polarity which acts as a functional equivalent, resulting in a silent alteration. Conservative substitutions for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Such chemokine derivatives can be made either by chemical peptide synthesis or by recombinant production from nucleic acid encoding the chemokine which nucleic acid has been mutated. Any technique for mutagenesis known in the art can be used, including but not limited to, chemical mutagenesis, in vitro site-directed mutagenesis (Hutchinson, C., et al., 1978, J. Biol. Chem 253:6551), use of TAB7 linkers (Pharmacia), etc.

In one embodiment, the only non-conservative amino acid substitutions in the RANTES derivatives of the invention are the substitution of leucine and isoleucine in place of the tyrosine residues at amino acid numbers 27 and 29 (Schall, 1991, Cytokine 3:165–183), respectively.

In another embodiment, the only non-conservative amino acid substitutions in the SDF-1 derivatives of the invention are the substitution of tyrosine in place of the leucine and isoleucine residues at amino acid numbers 28 and 30 (SWISS-PROT:P48061, Jun. 1, 1996), respectively.

In a specific embodiment, the chemokine, derivatives or analogs of the invention comprise the sequence Lys-Asn-X-Arg-Gln-Val (SEQ ID NO:5), where X is any amino acid, but is preferably asparagine or another polar neutral amino acid. A hexapeptide having the sequence of SEQ ID NO:5 is also provided.

Both β and α chemokines are active as monomers as well as dimers, and there is evidence that monomeric β chemokines can inhibit HIV infection and replication (DeVico et al., personal observation). It is therefore possible to construct a monomeric chimeric molecule that displays a wide range of receptor binding that will inhibit the infection or replication of a variety of HIV isolates. Accordingly, in a specific embodiment, the chemokine derivative or analog is a chimeric, or fusion, protein containing the polypeptide sequence of a chemokine that binds the chemokine receptor (preferably consisting of at least 5, 6, 7, 8, 9, 10, 15, 20, 30, 40, 50 60, 70 or 80 amino acids of the chemokine) joined at its amino- or carboxy-terminus via a peptide bond to an amino acid sequence of a different protein. In one embodiment, such a chimeric protein is produced by recombinant expression of a nucleic acid encoding the protein (comprising a chemokine amino acid sequence which binds the chemokine receptor joined in-frame to a coding sequence for a different protein). Such a chimeric product can be made by ligating the appropriate nucleic acid sequences encoding the desired amino acid sequences to each other by methods known in the art, in the proper coding frame, and expressing the chimeric product by methods commonly known in the art. Alternatively, such a chimeric product may be made by protein synthetic techniques, e.g., by use of a peptide synthesizer. In a specific embodiment, a chimeric nucleic acid encoding a chemokine with a heterologous signal sequence is expressed such that the chimeric protein is expressed and processed by the cell to the mature chemokine.

In a preferred embodiment, the chimeric of the invention comprises the amino acid sequence Lys-Asn-Asn-Asn-Arg-Gln-Val (SEQ ID NO:1) or Cys-Ala-Leu-Gln-Ile-Val-Ala-Arg-Leu-Lys-Asn-Asn-Asn-Arg-Gln-Val-Cys (SEQ ID NO:2) of mature SDF-1 joined at its amino- and/or carboxy-terminus via a peptide bond to a different protein. In another preferred embodiment, the chimeric comprises the amino acid sequence Lys-Asn-Arg-Gln-Val (SEQ ID NO:3) or Cys-Ser-Asn-Pro-Ala-Val-Val-Phe-Val-Thr-Arg-Lys-Asn-Arg-Gln-Val-Cys (SEQ ID NO:4) of mature RANTES (Schall, 1991, Cytokine 3:165–183) joined at its amino- and/or carboxy-terminus via a peptide bond to a different protein.

In other specific embodiments, the chimeric of the invention comprises a RANTES derivative wherein the amino acid sequence Lys-Asn-Asn-Asn-Arg-Gln-Val (SEQ ID NO:1) or Lys-Asn-X-Arg-Gln-Val (SEQ ID NO:5) is substituted for the sequence Lys-Asn-Arg-Gln-Val (SEQ ID NO:3) in RANTES, or the amino acid sequence Cys-Ala-Leu-Gln-Ile-Val-Ala-Arg-Leu-Lys-Asn-Asn-Asn-Arg-Gln-Val-Cys (SEQ ID NO:2) is substituted for the sequence Cys-Ser-Asn-Pro-Ala-Val-Val-Phe-Val-Thr-Arg-Lys-Asn-Arg-Gln-Val-Cys (SEQ ID NO:4) in RANTES. In other specific embodiments, the chimeric of the invention comprises a SDF-1 derivative wherein the amino acid sequence Lys-Asn-Arg-Gln-Val (SEQ ID NO:3) or Lys-Asn-X-Arg-Gln-Val (SEQ ID NO:5) is substituted for the sequence Lys-Asn-Asn-Asn-Arg-Gln-Val (SEQ ID NO:1) in SDF-1, or the amino acid sequence Cys-Ser-Asn-Pro-Ala-Val-Val-Phe-Val-Thr-Arg-Lys-Asn-Arg-Gln-Val-Cys (SEQ ID NO:4) is substituted for the sequence Cys-Ala-Leu-Gln-Ile-Val-Ala-Arg-Leu-Lys-Asn-Asn-Asn-Arg-Gln-Val-Cys (SEQ ID NO:2) in SDF-1. Molecules comprising or consisting of this chimeric sequence are provided, as are nucleic acids encoding the same.

In another embodiment, a chimeric of the invention contains those coding portions of two chemokines that bind to two distinct chemokine receptors. For example, a chimeric can be constructed which contains a nucleotide sequence encoding the amino acid sequence in RANTES that bind CC CKR-5 and a nucleotide sequence encoding the amino acid sequence of SDF-1 that bind CxC CKR4. The encoded protein of such a recombinant molecule could exhibit properties associated with both chemokines, and portray a novel profile of biological activities, including the ability to bind both chemokine receptors. In specific embodiments, such chimerics of the invention comprise a first amino acid sequence comprising Lys-Asn-Asn-Asn-Arg-Gln-Val (SEQ ID NO:1) or Cys-Ala-Leu-Gln-Ile-Val-Ala-Arg-Leu-Lys-Asn-Asn-Asn-Arg-Gln-Val-Cys (SEQ ID NO:2) of mature SDF-1 joined at its amino- or carboxy-terminal to a second amino acid sequence comprising Lys-Asn-Arg-Gln-Val (SEQ ID NO:3) or Cys-Ser-Asn-Pro-Ala-Val-Val-Phe-Val-Thr-Arg-Lys-Asn-Arg-Gln-Val-Cys (SEQ ID NO:4) of mature RANTES. Molecules comprising or consisting of this chimeric sequence are provided, as are nucleic acids encoding the same.

In additional embodiments, the chimeric of the invention comprises fragments of chemokines. In a specific embodiment the chimeric of the invention comprises a fragment of SDF-1 comprising the amino acid sequence Lys-Asn-Asn-Asn-Arg-Gln-Val (SEQ ID NO:1) or Cys-Ala-Leu-Gln-Ile-Val-Ala-Arg-Leu-Lys-Asn-Asn-Asn-Arg-Gln-Val-Cys (SEQ ID NO:2), wherein said SDF-1 fragment is less than 60 amino acids in length; fused via a covalent bond to an amino acid sequence comprising a fragment of RANTES comprising the amino acid sequence Lys-Asn-Arg-Gln-Val (SEQ ID NO:3) or Cys-Ser-Asn-Pro-Ala-Val-Val-Phe-Val-Thr-Arg-Lys-Asn-Arg-Gln-Val-Cys (SEQ ID NO:4), wherein said RANTES fragment is less than 55 amino acids in length. Optionally, one or both of the fragment components of this chimeric are capable of binding one or more chemokine receptors. Molecules comprising or consisting of this chimeric sequence are provided, as are nucleic acids encoding the same.

Chimeric chemokines of the invention may be synthetic peptide fragments or full length synthetic chemokines wherein are inserted specific sequences from α, β, and/or γ chemokines which optionally bind a chemokine receptor or inhibit immunodeficiency virus infection or replication, so as to bind one or more chemokine receptors. The primary sequence of the chemokines may also be used to predict tertiary structure of the molecules using computer simulation (Hopp and Woods, 1981, Proc. Natl. Acad. Sci. U.S.A. 78:3824–3828); chemokine/chemokine chimeric recombinant genes can be designed in light of correlations between tertiary structure and biological function.

Derivatives mentioned above also can be cyclized, e.g., as described herein.

Antiviral activity of the chemokines, nucleic acids encoding chemokines, or derivatives (including fragments and chimeric proteins) or analogs thereof, for treatment or prevention of HIV infection can be demonstrated by any of the methods disclosed in herein or known to one skilled in the art.

7.2 Preparation of Chemokines, Derivatives and Analogs

The chemokines. derivatives or analogs of the invention can be obtained commercially or alternatively, purified from biological tissue or cell culture, or produced by recombinant or synthetic techniques known in the art.

Native chemokine preparations can be obtained from a variety of sources. Recombinant RANTES, MIP-1α and MIP-1β are commercially available (Sigma Immunochemicals, St. Louis, Mo.; R&D Systems, Minneapolis, Minn; and PeproTech, Rocky Hills, N.J.). Alternatively, standard methods of protein purification may be used to isolate and purify, or partially purify, chemokines from any source known to contain or produce the desired chemokine, e.g., RANTES, MIP-1α, and MIP-1β may be isolated from sources such as $CD8^+$ T cells, HTLV-1, II transformed cell lines such as FC36.22, or uninfected immortalized cell lines. Such standard protein purification techniques include, but are not limited to, chromatography (e.g., ion exchange, affinity, gel filtration/molecular exclusion chromatography and reversed phase high performance liquid chromatography (RP-HPLC)), centrifugation, differential solubility, and electrophoresis (for a review of protein purification techniques, see, Scopes, Protein Purification; Principles and Procedure, 2nd Ed., C. R. Cantor, Editor, Springer Verlag, New York, N.Y. (1987), and Parvez et al., Progress in HPLC, Vol. 1, Science Press, (1985) Utrecht, The Netherlands). For example, antibodies to RANTES, MIP-1α, and MIP-1β are available commercially (e.g., Sigma Immunochemicals (St. Louis, Mo.); R&D Systems (Minneapolis. Minn.); and PeproTech, Inc. (Rocky Hills, N.J.)) and can be used to prepare an affinity chromatography column which can be used to purify the respective chemokines by well-known techniques (see, e.g., Hudson & May, 1986, Practical Immunology, Blackwell Scientific Publications, Oxford, United Kingdom).

Recombinant expression techniques can be applied to obtain the chemokines, derivatives, and analogs of the invention (see, e.g., Sambrook et al., 1989, Molecular Cloning, A Laboratory Manual, Cold Spring Harbor Laboratory, 2d Ed., Cold Spring Harbor, N.Y., Glover, D. M. (ed.), 1985, DNA Cloning: A Practical Approach, MRL Press, Ltd., Oxford, U.K., Vol. I, II). The nucleic acid sequences of the chemokines listed supra are known (for example, see, Rossi et al., 1997, J. Immunol. 158:1033–1036; Kitaura et al., 1996, J. Biol. Chem. 271:7725–7730; Ponath et al., 1996, J. Clin. Invest. 97:604–612; Hromas, R., Jan. 16, 1997, Genbank Accession Number U64197; Uguccioni et al., 1996, J. Exp. Med. 183:2379–2384; Baggiolini et al., 1994, Advances in Immunology 55:97–179; Miller and Krangel, 1992, Immunology 12:17–46; and Schall, 1991, Cytokine 3:165–183) and can be isolated using well-known techniques in the art, such as screening a library, chemical synthesis, or polymerase chain reaction (PCR). Other chemokines may be cloned using routine recombinant techniques known in the art in combination with assays which select for known biochemical properties of the chemokine of interest. Cloned chemokine gene sequence can be modified by any of numerous strategies known in the art.

To recombinantly produce a chemokines, chemokine derivatives and/or chemokine analogs, a nucleic acid sequence encoding the chemokine derivative or analog is operatively linked to a promoter such that the chemokine, derivative, or analog is produced from said sequence. For example, a vector can be introduced into a cell, wherein the vector or a portion thereof is expressed, producing a chemokine or a portion thereof. In a preferred embodiment, the nucleic acid is DNA if the source of RNA polymerase is DNA-directed RNA polymerase, but the nucleic acid may also be RNA if the source of polymerase is RNA-directed RNA polymerase or if reverse transcriptase is present in the cell or provided to produce DNA from the RNA. Such a vector can remain episomal or become chromosomally integrated, as long as it can be transcribed to produce the desired RNA. Such vectors can be constructed by recombinant DNA technology methods standard in the art.

A variety of host-vector systems may be utilized to express the protein-coding sequence. These include but are not limited to mammalian cell systems infected with virus (e.g., vaccinia virus, adenovirus, etc.); insect cell systems infected with virus (e.g., baculovirus); microorganisms such as yeast containing yeast vectors, or bacteria transformed with bacteriophage, DNA, plasmid DNA, or cosmid DNA. The expression elements of vectors vary in their strengths and specificities and depending on the host-vector system utilized, any one of a number of suitable transcription and translation elements may be used.

Expression of a chemokine protein, derivative, or analog may be controlled by any promoter/enhancer element known in the art. Such promoters include, but are not limited to: the SV40 early promoter region (Bernoist and Chambon, 1981, Nature 290:304–310), the promoter contained in the 3N long terminal repeat of Rous sarcoma virus (Yamamoto et al., 1980, Cell 22:787–797), the HSV-1 (herpes simplex virus-1) thymidine kinase promoter (Wagner et al., 1981, Proc. Natl. Acad. Sci. U.S.A. 78:1441–1445), the regulatory sequences of the metallothionein gene (Brinster et al., 1982, Nature 296:39–42); prokaryotic expression vectors such as the β-lactamase promoter (Villa-Kamaroff, et al., 1978, Proc. Natl. Acad. Sci. U.S.A. 75:3727–3731), or the tac promoter (DeBoer, et al., 1983, Proc. Natl. Acad. Sci. U.S.A. 80:21–25); see also "Useful proteins from recombinant bacteria" in Scientific American, 1980, 242:74–94; plant expression vectors comprising the nopaline synthetase promoter region (Herrera-Estrella et at., Nature 303:209–213) or the cauliflower mosaic virus 35S RNA promoter (Gardner, et al., 1981, Nucl. Acids Res. 9:2871), and the promoter of the photosynthetic enzyme ribulose biphosphate carboxylase (Herrera-Estrella et al., 1984, Nature 310:115–120); promoter elements from yeast or other fungi such as the Gal 4 promoter, the ADC (alcohol dehydrogenase) promoter, PGK (phosphoglycerol kinase) promoter, alkaline phosphatase promoter, and the following animal transcriptional control regions, which exhibit tissue specificity and have been utilized in transgenic animals: elastase 1 gene control region which is active in pancreatic acinar cells (Swift et al., 1984, Cell 38:639–646; Ornitz et al., 1986, Cold Spring Harbor Symp. Quant. Biol. 50:399–409; MacDonald, 1987, Hepatology 7:425–515); insulin gene control region which is active in pancreatic beta cells (Hanahan, 1985, Nature 315:115–122), immunoglobulin gene control region which is active in lymphoid cells (Grosschedl et al., 1984, Cell 38:647–658; Adames et al., 1985, Nature 318:533–538; Alexander et al., 1987, Mol. Cell. Biol. 7:1436–1444), mouse mammary tumor virus control region which is active in testicular, breast, lymphoid and mast cells (Leder et al., 1986, Cell 45:485–495), albumin gene control region which is active in liver (Pinkert et al., 1987, Genes and Devel. 1:268–276), alpha-fetoprotein gene control region which is active in liver (Krumlauf et al., 1985, Mol. Cell. Biol. 5:1639–1648; Hammer et al., 1987, Science 235:53–58; alpha 1-antitrypsin gene control region which is active in the liver (Kelsey et al., 1987, Genes and Devel. 1:161–171), beta-globin gene control region which is active in myeloid cells (Mogram et al., 1985, Nature 315:338–340; Kollias et al., 1986, Cell 46:89–94; myelin basic protein gene control region which is active in oligodendrocyte cells in the brain (Readhead et al., 1987, Cell 48:703–712); myosin light chain-2 gene control region which is active in skeletal muscle (Sani, 1985, Nature 314:283–286), and gonadotropic releasing hormone gene control region which is active in the hypothalamus (Mason et al., 1986, Science 234:1372–1378). The promoter element which is operatively linked to the nucleic acid encoding chemokines, chemokine derivatives and/or chemokine analogs can also be a bacteriophage promoter with the source of the bacteriophage RNA polymerase expressed from a gene for the RNA polymerase on a separate plasmid, e.g., under the control of an inducible promoter, for example, the nucleic acid encoding chemokine, derivative, or analog, operatively linked to the T7 RNA polymerase promoter with a separate plasmid encoding the T7 RNA polymerase.

In addition. a host cell strain may be chosen which modulates the expression of the inserted sequences, or modifies and processes the gene product in the specific fashion desired. Expression from certain promoters can be elevated in the presence of certain inducers; thus, expression of the genetically engineered chemokines, chemokine derivatives and/or chemokine analogs may be controlled. Furthermore, different host cells have characteristic and specific mechanisms for the translational and post-translational processing and modification (e.g., glycosylation, phosphorylation of proteins. Appropriate cell lines or host systems can be chosen to ensure the desired modification and processing of the foreign protein expressed. For example, expression in a bacterial system can be used to produce an unglycosylated core protein product. Expression in yeast will produce a glycosylated product. Expression in mammalian cells can be used to ensure "native" glycosylation of a heterologous protein. Furthermore, different vector/host expression systems may effect processing reactions to different extents.

The chemokine-encoding nucleic acid sequence can be mutated in vitro or in vivo, to create and/or destroy translation, initiation, and/or termination sequences, or to create variations in coding regions. Any technique for mutagenesis known in the art can be used, including but not limited to, in vitro site-directed mutagenesis (Hutchinson, C., et al., 1978, J. Biol. Chem 253:6551), use of TAB7 linkers (Pharmacia), etc.

The experimentation involved in mutagenesis consists primarily of site-directed mutagenesis followed by phenotypic testing of the altered gene product. Some of the more commonly employed site-directed mutagenesis protocols take advantage of vectors that can provide single stranded as well as double stranded DNA, as needed. Generally, the mutagenesis protocol with such vectors is as follows. A mutagenic primer, i e., a primer complementary to the sequence to be changed, but consisting of one or a small number of altered, added, or deleted bases, is synthesized. The primer is extended in vitro by a DNA polymerase and, after some additional manipulations, the now double-stranded DNA is transfected into bacterial cells. Next, by a variety of methods, the desired mutated DNA is identified, and the desired protein is purified from clones containing the mutated sequence. For longer sequences, additional cloning steps are often required because long inserts (longer than 2 kilobases) are unstable in those vectors. Protocols are known to one skilled in the art and kits for site-directed mutagenesis are widely available from biotechnology supply companies, for example from Amersham Life Science, Inc. (Arlington Heights, Ill. and Stratagene Cloning Systems (La Jolla, Calif.).

In other specific embodiments, the chemokine derivative or analog may be expressed as a fusion, or chimeric protein product (comprising the protein, fragment, analog, or derivative joined via a peptide bond to a heterologous protein sequence (of a different protein)). Such a chimeric product can be made by ligating the appropriate nucleic acid sequences encoding the desired amino acid sequences to each other by methods known in the art, in the proper coding frame and expressing the chimeric product by methods commonly known in the art.

In addition, chemokines, derivatives (including fragments and chimeric proteins), and analogs can be chemically synthesized. See, e.g, Clark-Lewis et al., 1991, Biochem. 30:3128–3135 and Merrifield, 1963, J. Amer. Chem. Soc. 85:2149–2156. For example, chemokines, derivatives and analogs can be synthesized by solid phase techniques, cleaved from the resin, and purified by preparative high performance liquid chromatography (e.g., see Creighton, 1983, Proteins, Structures and Molecular Principles, W.H. Freeman and Co., N.Y., pp. 50–60). Chemokines, derivatives and analogs can also be synthesized by use of a peptide synthesizer. The composition of the synthetic peptides may be confirmed by amino acid analysis or sequencing (e.g., the Edman degradation procedure; see Creighton, 1983, Proteins, Structures and Molecular Principles, W.H. Freeman and Co., N.Y., pp. 34–49). Furthermore, if desired, nonclassical amino acids or chemical amino acid analogs can be introduced as a substitution or addition into the chemokines, chemokine derivatives and/or chemokine analogs. Non-classical amino acids include but are not limited to the D-isomers of the common amino acids, 2,4-diaminobutyric acid, α-amino isobutyric acid, 4-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, β-alanine, fluoro-amino acids, designer amino acids such as β-methyl amino acids, Cα-methyl amino acids, Nα-methyl amino acids, and amino acid analogs in general. Furthermore, the amino acid can be D (dextrorotary) or L (levorotary).

By way of example but not by way of limitation, proteins (including peptides) of the invention can be chemically synthesized and purified as follows: chemokines, derivatives and analogs can be synthesized by employing the N-α-9-fluorenylmethyloxycarbonyl or Fmoc solid phase peptide synthesis chemistry using a Rainin Symphony Multiplex Peptide Synthesizer. The standard cycle used for coupling of an amino acid to the peptide-resin growing chain generally includes: (1) washing the peptide-resin three times for 30 seconds with N,N-dimethylformamide (DMF); (2) removing the Fmoc protective group on the amino terminus by deprotection with 20% piperdine in DMF by two washes for 15 minutes each, during which process mixing is effected by bubbling nitrogen through the reaction vessel for one second every 10 seconds to prevent peptide-resin settling; (3) washing the peptide-resin three times for 30 seconds with DMF; (4) coupling the amino acid to the peptide resin by addition of equal volumes of a 250 -mM solution of the Fmoc derivative of the appropriate amino acid and an activator mix consisting or 400 mM N-methylmorpholine and 250 mM (2-(1H-benzotriazol-1-4))-1,1,3,3-tetramethyluronium hexafluorophosphate (HBTU) in DMF; (5) allowing the solution to mix for 45 minutes; and (6) washing the peptide-resin three times for 30 seconds of DMF. This cycle can be repeated as necessary with the appropriate amino acids in sequence to produce the desired polypeptide. Exceptions to this cycle program are amino acid couplings predicted to be difficult by nature of their hydrophobicity or predicted inclusion within a helical formation during synthesis. For these situations, the above cycle can be modified by repeating step 4 a second time immediately upon completion of the first 45 minute coupling step to "double couple" the amino acid of interest. Additionally, in the first coupling step in polypeptide synthesis, the resin can be allowed to swell for more efficient coupling by increasing the time of mixing in the initial DMF washes to three 15 minute washes rather than three 30 second washes. After polypeptide synthesis, the peptide can be cleaved from the resin as follows: (1) washing the polypeptide-resin three times for 30 seconds with DMF; (2) removing the Fmoc protective group on the amino terminus by washing two times for 15 minutes in 20% piperdine in DMF; (3) washing the polypeptide-resin three times for 30 seconds with DMF; and (4) mixing a cleavage cocktail consisting of 95% trifluoroacetic acid (TFA), 2.4% water, 2.4% phenol, and 0.2% triisopropysilane with the polypeptide-resin for two hours, then filtering the peptide in the cleavage cocktail away from the resin, and precipitating the peptide out of solution by addition of two volumes of ethyl ether. To isolate the polypeptide, the ether-peptide solution can be allowed to sit at −20EC for 20 minutes, then centrifuged at 6,000×G for 5 minutes to pellet the polypeptide, and the polypeptide can be washed three times with ethyl ether to remove residual cleavage cocktail ingredients. The final polypeptide product can be purified by reversed phase high pressure liquid chromatography (RP-HPLC) with the primary solvent consisting of 0.1% TFA and the eluting buffer consisting of 80% acetonitrile and 0.1% TFA. The purified polypeptide can then be lyophilized to a powder.

In one embodiment, the polypeptide is a cyclic peptide. Cyclized polypeptides can be prepared by any method known in the art. For example, but not by way of limitation, disulfide bridge formation can be achieved by (1) dissolving the purified peptide at a concentration of between 0.1.–0.5 mg/ml in 0.01 M ammonium acetate. pH 7.5; (2) adding 0.01 M potassium ferricyanide to the dissolved peptide dropwise until the solution appears pale yellow in color and allowing this solution to mix for 24 hours; (3) concentrating the cyclized polypeptide to 5–10 ml of solution, repurifying the polypeptide by reverse phase-high pressure liquid chromatography (RP-HPLC) and finally lyophilizing the polypeptide. In a specific embodiment, wherein the polypeptide does not contain two appropriately situated cysteine residues, cysteine residues can be introduced at the amino-terminus and/or carboxy-terminus and/or internally such that the polypeptide to be cyclized contains two cysteine residues spaced such that the residues can form a disulfide bridge. Alternatively, a cyclic polypeptide can be obtained by generating an amide linkage. An amide linkage can be achieved by, for example, but not limited to, the following procedure: An allyl protected amino acid, such as aspartate, glutamate, asparagine or glutamine, can be incorporated into the polypeptide as the first amino acid, and then the remaining amino acids coupled on. The allyl protective group can be removed by a two hour mixing of the polypeptide-resin with a solution of tetrakistriphenylphophine palladium (0) in a solution of chloroform containing 5% acetic acid and 2.5% N-methylmorpholine. The polypeptide resin can be washed three times with 0.5% N,N-diisopropylethylamine (DIEA) and 0.5% sodium diethyldithiocabamate in DMF. The amino terminal Fmoc group on the polypeptide chain can be removed by two incubations for 15 minutes each in 20% piperdine in DMF, and washed three times with DMF for 30 seconds each. The activator mix, N-methylmorpholine and HBTU in DMF, can be brought onto the column and allowed to couple the free amino terminal end to the carboxyl group generated by removal of the allyl group to cyclize the polypeptide. The polypeptide can cleaved from the resin as described in the general description of chemical polypeptide synthesis above and the polypeptide purified by reverse phase-high pressure liquid chromatography (RP-HPLC). In a specific embodiment, wherein the polypeptide to be cyclized does not contain an allyl protected amino acid, an allyl protected amino acid can be introduced into the sequence of the polypeptide, at the amino-terminus, carboxy-terminus or internally, such that the polypeptide can be cyclized.

In another embodiment, a polypeptide that is a chemokine or derivative thereof is synthesized to contain disulfide brides corresponding to those observed in the native chemokine. Techniques known in the art may be applied to achieve selective disulfide bridge formation, including but not limited to the use of cysteine residues that having different protection groups. For example, full length RANTES may be synthesized as described above, but incorporating acetamidomethyl (Acm) protected cysteine amino acids at positions 10 and 37 of the polypeptide. After synthesis is completed, the polypeptide is cleaved off the support resin. The cleavage, deprotection reaction is for 2 hours in 88% trifluoracetic acid, 5% water, 5% phenol, and 2% triisopropylsilane. This step additionally deprotects the initial trityl groups from Cys11 and Cys50. The polypeptides are purified by reverse phase HPLC to >95% purity. The polypeptide is diluted in 0.1M NaOH, pH 8.0 at a concentration of 0.25 mg/ml and allowed to mix 24 hours at room temperature to create a disulfide bridge between amino acids Cys11 and Cys50. Disulfide linked polypeptide is repurified by reverse phase HPLC. The polypeptide is dissolved in 80% acetic acid at a concentration of 0.25 mg/ml and solid iodine is added at a concentration of 0.25 mg/ml and allowed to mix for 24 hours at room temperature. This step deprotects the Acm groups from Cys10 and Cys34 amino acids to form the final disulfide bridge. An equal volume of water is added to the mixture which is extracted four times with 50 mls of $CCl_4$ to remove the iodine. The product, now containing disulfide bridges between amino acids Cys11 and Cys50 and between amino acids Cys10 and Cys34, is lyophilized.

The chemokines, derivatives, or analogs of the invention may be synthesized in their entirety by the sequential addition of amino acid residues or alternatively as fragment subcomponents which may be combined using techniques well known in the art, such as, for example, fragment condensation (Shin et al., 1992, Biosci. Biotech. Biochem. 56:404–408; Nyfeler et al., 1992, Peptides, Proc. 12th Amer. Pep. Soc., Smith and Rivier (eds), Leiden, pp 661–663); and Nokihara et al., 1990, Protein Research Foundation, Yanaihara (ed), Osaka, pp 315–320).

Also included within the scope of the invention are chemokines, derivatives, and analogs which are differentially modified during or after synthesis, e.g., by benzylation, glycosylation, acetylation, phosphorylation, amidation, pegylation, derivatization by known protecting/ blocking groups, proteolytic cleavage, linkage to an antibody molecule or other cellular ligand, etc. In specific embodiments, the chemokines, derivatives, or analogs are acetylated at the N-terminus and/or amidated at the C-terminus. Any of numerous chemical modifications may be carried out by known techniques, including but not limited to acetylation, formylation, oxidation, reduction; metabolic synthesis in the presence of tunicamycin; etc. These modifications may serve to increase the stability, bioavailability and/or inhibitory action of the peptides of the invention.

In a less preferred embodiment, chemokine derivatives can be obtained by proteolysis of the chemokine followed by purification using standard methods such as those described above (e.g., immunoaffinity purification).

Any of the chemokines, derivatives or analogs described above may, additionally, have a non-peptide macromolecular carrier group covalently attached to its amino and/or carboxy termini. Such macromolecular carrier groups may include, for example, lipid-fatty acid conjugates or carbohydrates.

7.3 Assays for Receptor Binding and Inhibition of Viral Infection or Replication by Chemokine Proteins, Derivatives and Analogs The ability of chemokines or the derivatives or analogs thereof to bind chemokine receptors and thereby interfere with viral infection or replication can be assayed by various methods.

In a preferred embodiment, the chemokine derivatives (including fragments and chimeric proteins) or analogs, bind protein sequences contained in the extracellular domain of a chemokine receptor. Binding can be assayed by means well-known in the art. For example, bioassays may be performed wherein cells known to be expressing a chemokine receptor are exposed to the chemokine derivative or analog to be tested and assayed for a known effect (e.g., signal transduction). Alternatively, chemokines, derivatives or analogs can be tested for the ability to bind chemokine receptors by procedures, including but not limited to, protein affinity chromatography, affinity blotting, immunoprecipitation, cross-linking, and library based methods such as protein probing, phage display, and the two-hybrid system (see, generally, Phizicky et al., 1995, Microbiol. Rev. 59:94–123). Further. where DNA encoding a chemokine receptor has been identified, this sequence may be routinely manipulated in known assays to identify chemokine derivatives or analogs which bind to the extracellular domain of the receptor. Such assays include, but are limited to, in vitro cell aggregation and interaction trap assays. Nucleic acids encoding CC CKR-1 (Neote et al., 1993, Cell 72:415–425); CC CKR-2A and CC CKR-2B (Chavo et al., 1994, Proc. Natl. Acad. Sci. 91:2752–2756); CC CKR-3 (Daugherty et al., 1996, J. Exp. Med. 183:2349–2354 and Ponath et al., 1996, J. Exp. Med. 183:1–12); CC CKR-4 (Power et al., 1995, J. Biol. Chem. 270:19495–19500); CC CKR-5 (Samson et al., 1996, Biochemistry 35:3362–3367); CxC CKR4 (Feng et al., 1996, Science 272:872–877); IL-8RA and IL-8RB (Kunz et al., 1991, J. Biol. Chem. 267:9101–9106 and Gerard et al., 1994, Corr. Opin. Immunol. 6:140–145); Duffy antigen (Horuk et al., 1994, J. Biol. Chem. 269:1770–1773; Neote et al., 1994, Blood 84:44–52; and Neote et al., 1993, J. Biol. Chem. 268:12247–12249); and Mig receptor and γIP-10 receptor (Loestcher et al., 1996, J. Exp. Med. 184(3):963–969) have been isolated and cloned.

High throughput screening for chemokines, chemokine derivatives and/or chemokine analogs receptor binding may be performed by methods known in the art, including but not limited to flow cytometry. According to this method, cells that express human CD4 and one of the HIV co-receptors (e.g., CC CKR-5, CxC CKR4, etc.) are treated with biotinylated chemokine, derivative, or analog and cell surface binding to each cell type is detected with an avidin FITC conjugate. Alternatively, other methods for labeling or detecting binding of the chemokines, chemokine derivatives and/or chemokine analogs, such as antibodies, may be used. The same flow cytometry system may be used to assess receptor binding specificity, by testing for competitive binding between the chemokines, chemokine derivatives and/or chemokine analogs and known ligands.

The antiviral activity exhibited by the chemokine, derivative and/or analog of the invention may be measured, for example, by easily performed in vitro assays, which can test the compound's ability to inhibit syncytia formation or to inhibit infection by cell-free virus and assess the effects of the compound on cell proliferation and viability. Applying these assays, the relative antiviral activity that a chemokine, derivative and/or analog exhibits against a given virus or strain of immunodeficiency virus and chemokine, derivative, and/or analog combination formulation best suited for viral and strain specific inhibitory activity can be determined.

In one embodiment, a cell fusion assay is used to test the ability of chemokines, chemokine derivatives and/or chemokine analogs, to inhibit HIV-induced syncytia formation in vitro. Such an assay involves culturing uninfected $CD4^+$ cells in the presence of chronically HIV-infected cells and the composition containing a chemokines, chemokine derivatives and/or chemokine analogs to be assayed. For each, a range of concentrations may be tested. This range should include a control culture wherein no chemokine, derivative and/or analog has been added. Standard conditions for culturing, well known to those of ordinary skill in the art, are used. After incubation for an appropriate period, such as, for example, 24 hours at 37EC, the culture is examined microscopically for the presence of multinucleated giant cells, which are indicative of cell fusion and syncytia formation.

In one embodiment, an in vitro cell-free infectivity assay is performed using primary macrophages and the macrophage-tropic isolate HIV-$1_{BaL}$, the first described macrophage-tropic HIV-1 isolate (see, Gartner et al., 1986, Science 233:215). According to this assay, primary macrophage cells isolated according to methods known in the art are infected with HIV-$1_{BaL}$ that has been propagated and maintained only in primary macrophages. The input immunodeficiency virus is incubated with primary macrophages in the presence of concentrations of the chemokine, derivative, or analog to be tested. After a defined period of infection, unbound virus is removed by washing, and the cells are placed in culture. The level of virus replication in this assay may be assessed by techniques known in the art, including but not limited to, measuring reverse transcriptase (RT) levels, or the release of extracellular p24 core antigen at different days post-infection. A constant level of inhibition of viral infection or replication is determined by measuring output HIV p24 levels (or another indicator of viral infection or replication, such as for example, RT) relative to control assays performed in the absence of the chemokines, chemokine derivatives and/or chemokine analogs. Preferably, the chemokine derivative or analog reduces levels of virus, as measured by, for example, p24, by ∃ 50% relative to control assays carried out in the absence of test compound. The presence of p24 may be determined using methods known in the art, such as commercially available enzyme-linked immunosorbent assays (Coulter, Hialeah, Fla.; Abbott Laboratories, Hvalstad, Norway). Alternatively, RT activity may be tested by monitoring cell-free supernatant using standard techniques such as those described by, for example, Goff et al. (Goff et al., 1981, J. Virol. 38:239–248) and Willey et al. (Willey et al., 1988, J. Virol. 62:139–147).

In addition to evaluating the antiviral activity of a chemokines, chemokine derivatives and/or chemokine analogs, the primary macrophage/HIV-1$_{BaL}$ cell-free infectivity assay test system may also be used to determine the ability of combinations of chemokines, derivatives, and/or analogs to suppress HIV infection or replication. Furthermore, the assay may routinely be modified to use other macrophage-tropic strains that have been propagated and maintained in macrophages to identify chemokines, derivatives and/or analogs effective in inhibiting infection or replication of one or multiple M-tropic viral isolates.

In a preferred embodiment, an in vitro cell-free infectivity assay is performed using activated primary CD4$^-$ peripheral blood mononuclear cells (PBMC's) that have been isolated according to methods known in the art; such as for example, (+) or (–) selection by immunomagnetic beads (Dynal A. S., Norway) and Ficoll gradient centrifugation. Techniques for activating primary PBMC with such compounds as phytohemagglutinin (PHA) or the monoclonal antibody OKT3 are also known in the art (see, e.g., Cocchi et al., 1995, Science, 270:1811–1815). The activated primary PBMC are incubated with 10–50 TCID$_{50}$ (half-maximal tissue-culture infectious dose) primary syncytia-inducing or non-syncytia-inducing, T-tropic, viral stocks that have been obtained from the NIH AIDS Research and Reference Reagent Program or isolated according to methods known in the art, such as for example, that described in herein. Primary virus stocks may also be generated from lymph node T cells (via lymph node aspirate or biopsy). The procedure for isolating virus from lymph node material is the same as that used to isolate virus from PBMC's.

As above, the input immunodeficiency virus is incubated with target cells in the presence of various quantities of the test chemokine, derivative, or analog to be tested. After a defined period of infection, unbound virus is removed by washing, and the cells are placed in culture. As above, the level of virus replication in this assay may be assessed by techniques known in the art, including but not limited to, measuring reverse transcriptase levels or the release of extracellular p24 core antigen at different days post-infection. A constant level of inhibition of viral infection or replication is determined by measuring output HIV p24 levels (or another indicator) relative to control assays performed in the absence of the chemokines, chemokine derivatives and/or chemokine analogs. Preferably, the chemokine derivative or analog reduces levels of virus, as measured by, for example, p24, by ∃ 50% relative to control assays carried out in the absence of test compound.

In addition to evaluating the antiviral activity of a chemokines, chemokine derivatives and/or chemokine analogs, the primary CD4$^+$ PBMC/HIV-1 assay may be used to formulate pharmaceutical compositions containing combinations of chemokines, derivatives, and/or chemokine analogs, effective in inhibiting infection or replication of the viral isolates assayed and may be applied to formulate a pharmaceutical composition effective in inhibiting infection or replication of a plurality of T-tropic strains.

In an additional embodiment, an in vitro cell-free infectivity assay is performed using PM1 cells and HIV$_{BaL}$. As above, the input immunodeficiency virus is incubated with target cells (PM1) in the presence of various quantities of the test chemokine, derivative, or analog to be tested. After a defined period of infection, unbound virus is removed by washing, and the cells are placed in culture. As above, the level of immunodeficiency virus replication in this assay may be assessed by techniques known in the art, including but not limited to, measuring reverse transcriptase levels or the release of extracellular p24 core antigen at different days post-infection. A constant level of inhibition of viral infection or replication is determined by measuring output HIV p24 levels (or another indicator) relative to control assays performed in the absence of the chemokines, chemokine derivatives and/or chemokine analogs. Preferably, the chemokine derivative or analog reduces levels of virus, as measured by, for example, p24, by ∃ 50% relative to control assays carried out in the absence of test compound.

In another embodiment, an assay is performed using cells from HIV$^+$ individuals. According to this assay, HIV$^+$ CD4$^+$ peripheral blood cells are recovered from an infected individual using techniques known in the art and incubated in the presence and absence of test chemokines, chemokine derivatives and/or chemokine analogs. Optionally, the cells are co-cultured with uninfected allogeneic CD4$^+$ PBMC's. According to this assay, the input immunodeficiency virus is incubated with target cells in the presence of various concentrations of the test chemokine, derivative, or analog that are maintained throughout culture. Culture supernatant samples are removed periodically (every 1–3 days) and tested for virus expression by techniques known in the art, such as by measuring the release of extracellular p24 core antigen, or another indicator of viral infection or replication, at different days post-infection. Virus is usually detected by day 7 of culturing. A constant level of inhibition of viral infection or replication is determined relative to control assays performed in the absence of the chemokines, chemokine derivatives and/or chemokine analogs. For many individuals with advanced infection. CD4$^+$ cell levels are very low. In these cases, CD4$^+$ cells isolated from the HIV$^+$ individual are optionally incubated with uninfected CD4$^+$ target cells. This assay models the rapid viral replication and cytopathic effects contributing to the loss of CD4$^+$ cells in vivo by utilizing primary target cells and primary viral isolates and is exemplified herein. In addition to evaluating the antiviral activity of a chemokines, chemokine derivatives and/or chemokine analogs, this assay may be used to determine the ability of combinations of chemokines, derivatives and/or analogs to inhibit transmission of isolates specific to the patient at a given time.

In another embodiment, chemokine(s), derivative(s) and/or analog(s) are identified by their ability to inhibit the isolation of primary immunodeficiency virus isolates from primary target cells removed from an infected individual. According to this embodiment, CD4$^+$ target cells isolated from an HIV$^+$ individual using techniques known in the art are exposed to one or more chemokines, derivatives, and/or analogs and known techniques, such as those described infra, are applied to isolate the virus from the cells. In a preferred embodiment, these chemokines, derivatives and/or analogs are known or indicated by the in vitro assays described herein to inhibit the infection or replication of one or more HIV-1 strains. Parallel control experiments are performed wherein the same virus isolation technique is performed in the absence of chemokines, derivatives, and/or analogs. An inability or reduced ability to isolate immunodeficiency virus in the test samples, but not the control sample indicates that the primary immunodeficiency virus isolates are sensitive to the test chemokines, derivatives, and/or analogs.

The chemokine protein, derivative, or analog compositions may then be combined with suitable pharmaceutically acceptable carriers and administered by techniques known in the art, such as those described herein.

Techniques known in the art may be applied to formulate compositions displaying minimal toxicity. For each in vitro test of chemokines, derivatives and/or analogs of the invention, it is important to determine the effects on cell proliferation and viability. Methods for assessing effects of the compounds tested on cell proliferation include, but are not limited to, assaying for thymidine uptake and counting cells (using, for example, a hemocytometer or flow cytometer). Methods for assessing cell viability include, but are not limited to, trypan blue dye exclusion. In a specific embodiment, an assay is performed wherein the proliferative response of stimulated target cells to a range of concentrations of the test composition(s) is assessed by monitoring [$^3$H]-Thymidine incorporation.

Other methods for assaying the antiviral activity of chemokines, derivatives and/or analogs will be known to the skilled artisan and are within the scope of the invention.

The assays described herein may be applied to routinely predict which chemokines, chemokine derivatives and/or chemokine analogs will display an antiviral effect in vivo and the optimal concentration for doing so. Chemokines, derivatives, and analogs displaying anti-viral activity are optionally combined.

The in vitro assays described herein can further be applied to screen numerous primary and established viral isolates with chemokines, derivatives, and/or analogs for formulation of a pharmaceutical composition containing as active ingredients, chemokines, derivatives, and/or analogs that are able to inhibit infection or replication of a plurality of viral isolates. In a specific embodiment, this pharmaceutical composition inhibits infection or replication of at least 3, 4, 5, 6, 7, 8, 9, 10, 15, or 20 distinct immunodeficiency virus isolates. While the pharmaceutical composition formulated according to this method is ideally suited for prophylactic administration, therapeutic administration of the pharmaceutical composition is also envisioned.

The invention provides for treatment or prevention of diseases and disorders associated with infection by an immunodeficiency virus, particularly, HIV, by administration of a therapeutic compound ("therapeutic"). The therapeutics of the invention are as described herein, e.g., chemokines and therapeutically and/or prophylactically effective chemokine derivatives and/or analogs, i.e., those derivatives and analogs which prevent or treat HIV infection (e.g. as demonstrated in vitro assays described infra), as well as nucleic acids encoding such chemokines, derivatives and analogs thereof.

The invention also provides methods for treating or preventing viral infections, by administering an effective amount of a therapeutic of the invention that binds to one or more chemokine receptors. In one embodiment, the therapeutic is a chemokine, derivative, or analog that binds to an α and β chemokine receptor. In further embodiments, the therapeutic is a chemokine, chemokine derivative and/or chemokine analog that binds to 3, 4, 5, 6, 7, 8, 9, or 10 chemokine receptors. In a preferred embodiment, the therapeutic is able to bind CC CKR-5 and CxC CKR4. In another embodiment, the pharmaceutical composition contains a plurality of therapeutic chemokines, derivatives, and/or analogs.

The therapeutics of the invention can also be tested in vivo for toxicity and/or the desired therapeutic or prophylactic activity. For example, such compounds can be tested in suitable animal models including but not limited to rats, mice, chickens, cows, sheep, dogs, cats, monkeys, apes, rabbits, etc. For in vivo testing, prior to administration to humans, any animal model system known in the art may be used.

7.4 Formulating a Patient-Specific Pharmaceutical Composition

In particular embodiments, the invention provides methods for formulating a pharmaceutical composition which comprises the chemokines, derivatives, and/or analogs that inhibit replication and/or infection of immunodeficiency virus isolate(s) found in an individual at a given time and preferably does not comprise chemokines or derivatives and/or analogs thereof that do not inhibit replication and/or infection of such isolate(s). Such methods are achieved by isolating primary immunodeficiency virus(es) from PBMC's and/or lymph nodes of a patient, and testing the virus(es) against a panel of chemokines (or derivatives or analogs thereof) to determine which particular chemokines are active in inhibiting the infection and/or replication of such viral isolate(s). The chemokines thereby that are identified as having activity in inhibiting replication and/or infection of the immunodeficiency virus isolate(s) are then used as components of a pharmaceutical composition comprising them to treat the patient.

The ability to formulate a therapeutic composition to contain only those chemokines, derivatives, and/or analogs that are effective in inhibiting viral infection or replication in the patient and further, to contain only those compounds demonstrating high viral infection or replication inhibiting activity is extremely valuable since the risk of serious side effects increases with chemokine concentration.

Techniques that can be used for isolating a primary immunodeficiency virus from PBMC's and/or lymph nodes of a patient are known in the art. In one embodiment, primary viruses are propagated in allogeneic CD4$^+$ PBMC's prior to isolation, and then tested in in vitro assays, such as those described infra which use primary macrophages and CD4$^+$ PBMC's as target cells, for inhibiting viral infection or replication in the presence of chemokines, derivatives and/or analogs. In specific embodiments, the immunodeficiency virus isolate is HIV.

Once a immunodeficiency virus is isolated, the ability of one, two, three, or more, preferably a panel of at least 5 chemokines, derivatives, and/or analogs to inhibit infection or replication of the isolate may be tested according to the assays described herein. Chemokines, derivatives, and analogs found to be effective at inhibiting infection or replication of the immunodeficiency virus isolate are preferably then tested over a range of concentrations to determine optimum antiviral concentrations using techniques known in the art.

In a specific embodiment, the pharmaceutical composition of the invention comprises a plurality of chemokines, derivatives, and/or analog determined to be effective in inhibiting infection and/or replication of an immunodeficiency virus isolate of interest. In particular the pharmaceutical composition comprises 2, 3, 4, 5, 6, 7, 8, 9, or 10 chemokines, derivatives, and or analogs determined to have antiviral activity. Assays described infra, may be used to determine optimum relative concentrations of the chemokine, derivative, and/or analog components of the pharmaceutical composition.

The invention therefore provides methods by which to identify chemokine(s), derivative(s), or analog(s) that inhibit infection or replication of a specific isolate of an immunodeficiency virus, particularly an HIV-1 isolate, and by which pharmaceutical compositions containing these chemokines or therapeutically or prophylactically effective derivatives, or analogs, alone or in combination, are routinely formulated. The invention further provides methods for treating or preventing immunodeficiency virus infections, in particular HIV infection, in mammals, including humans, by administering the therapeutic compositions of the invention.

The invention thus provides methods for formulating on a patient-to-patient basis, a pharmaceutical composition comprising chemokines, derivatives and/or analogs that are known to be effective against isolate(s) of an immunodeficiency virus present in an individual at a given time.

7.5 Therapeutic Uses

The invention provides for treatment or prevention of diseases and disorders associated with infection by an immunodeficiency virus, particularly, HIV, by administration of a therapeutic of the invention. Such therapeutics include, but are not limited to: chemokines and therapeutically and prophylactically effective chemokine derivatives and/or analogs, i.e., those derivatives and analogs which prevent or treat HIV infection (e.g. as demonstrated in vitro assays described infra), as well as nucleic acids encoding such chemokines, derivatives and analogs thereof (e.g., for use in gene therapy). Examples of therapeutics are those chemokines, derivatives and analogs described herein and nucleic acids encoding such proteins. Preferred assays to determine the utility of a specific therapeutic and whether its administration is indicated for treatment are described herein.

A preferred embodiment of the invention is directed to methods of using a therapeutic for treatment and prevention of HIV infection, preferably HIV-1 infection, in a human subject.

Therapeutic compositions of the invention have application in treating and preventing disorders associated with immunodeficiency viruses, including but not limited to types of HIV, e.g., HIV-1and HIV-2. A preferred embodiment of the invention relates to methods of using a therapeutic for treatment or prevention of HIV infection, preferably HIV-1, in a human subject. In the treatment of HIV infection, the therapeutic of the invention can be used to prevent progression of HIV-1 infection to acquired immune deficiency syndrome AIDS or to AIDS-related complex (ARC) in a human patient, or to treat a human patient with ARC or AIDS.

Therapeutic compositions of the invention also have application in treating and preventing disorders associated with non-human immunodeficiency viruses, including but not limited to simian immunodeficiency virus.

In vitro assays which can be used to determine whether administration of a specific composition containing one or more chemokines, derivatives or analogs, inhibits viral infection or replication are discussed infra. These assays can indicate which chemokine, derivative, or analog has the desired therapeutic efficacy in inhibiting infection or replication of a particular viral isolate and additionally may be used to formulate the appropriate pharmaceutical combination of chemokines, derivatives, and/or analogs that demonstrates antiviral activity against one or multiple viral strains.

In a specific embodiment, the therapeutic method of the invention is carried out as monotherapy, i.e., as the only agent provided for treatment or prevention of HIV. In another embodiment, the therapeutic is administered in combination with one or more anti-viral compounds, for example, protease inhibitors (e.g., sequinavir) and/or reverse transcriptase inhibitors (e.g., azidothymidine (AZT), lamioridine (3TC), dideoxyinosine (ddI), dideoxycytidine (ddC)). The therapeutic may also be administered in conjunction with chemotherapy (e.g., treatment with adriamycin, bleomycin, vincristine, vinblastine, doxorubicin and/or Taxol) or other therapies known in the art.

7.5.1 Gene Therapy

In a specific embodiment, nucleic acids comprising a sequence encoding chemokine, protein derivative or protein analog, effective at inhibiting HIV replication and/or infection in vitro are administered for treatment or prevention of HIV infection, by way of gene therapy. Gene therapy refers to therapy performed by the administration of a nucleic acid to a subject. In this embodiment of the invention, the nucleic acid produces its encoded protein that mediates a therapeutic effect by preventing or treating HIV infection. For example, any of the methods for gene therapy available in the art can be used according to the present invention. Exemplary methods are described below.

For general reviews of the methods of gene therapy, see Goldspiel et al., 1993, Clinical Pharmacy 12:488–505; Wu and Wu, 1991, Biotherapy 3:87–95; Tolstoshev, 1993, Ann. Rev. Pharmacol. Toxicol. 32:573–596; Mulligan, 1993, Science 260:926–932; and Morgan and Anderson, 1993, Ann. Rev. Biochem. 62:191–217: May, 1993, TIBTECH 11(5):155–215. Methods commonly known in the art of recombinant DNA technology which can be used are described in Ausubel et al. (eds.), 1993, Current Protocols in Molecular Biology, John Wiley & Sons, NY; and Kriegler, 1990, Gene Transfer and Expression, A Laboratory Manual, Stockton Press, NY.

In a preferred aspect, the nucleic acid encoding chemokines, chemokine derivatives and/or chemokine analogs is part of an expression vector that produces chemokines, chemokine derivatives and/or chemokine analogs in a suitable host. In particular, such a nucleic acid has a promoter operably linked to the nucleic acid sequence coding for chemokines, chemokine derivatives and/or chemokine analogs, said promoter being inducible or constitutive, and, optionally, tissue-specific. In another particular embodiment, a nucleic acid molecule is used wherein the chemokine, derivative, or analog sequences and any other desired sequences are flanked by regions that promote homologous recombination at a desired site in the genome, thus providing for intrachromosomal expression of chemokine, derivative, or analog (Koller and Smithies, 1989, Proc. Natl. Acad. Sci. USA 86:8932–8935; Zijlstra et al., 1989, Nature 342:435–438).

Delivery of the nucleic acid into a patient may be either direct, wherein case the patient is directly exposed to the nucleic acid or nucleic acid-carrying vector, or indirect, wherein case, cells are first transformed with the nucleic acid in vitro, then administered to the patient. These two approaches are known, respectively, as in vivo or ex vivo gene therapy.

In a specific embodiment, the nucleic acid is directly administered in vivo, where it is expressed to produce the encoded product. This can be accomplished by any of numerous methods known in the art, e.g., by constructing it as part of an appropriate nucleic acid expression vector and administering it so that it becomes intracellular, e.g., by infection using a defective or attenuated retroviral or other viral vector (see U.S. Pat. No. 4,980,286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering it in linkage to a peptide which is known to enter the cell or nucleus, e.g., by administering it in linkage to a ligand subject to receptor-mediated endocytosis (see e.g., Wu and Wu, 1987, J. Biol. Chem. 262:4429–4432) (which can be used to target cell types specifically expressing the receptors), etc. In a specific embodiment, the nucleic acid can be targeted in vivo for cell specific uptake and expression, by targeting a specific receptor (see, e.g., PCT Publications WO 92/06180 dated Apr. 16, 1992 (Wu et al.); WO 92/22635 dated Dec. 23, 1992 (Wilson et al.); WO 92/20316 dated Nov. 26, 1992 (Findeis et al.); WO 93/14188 dated Jul. 22, 1993 (Clarke et al.), WO 93/20221 dated Oct. 14, 1993 (Young)). In another embodiment, a nucleic acid-ligand complex can be formed wherein the ligand comprises a fusogenic viral peptide to disrupt endosomes, allowing the nucleic acid to avoid lysosomal degradation Alternatively, the nucleic acid can be introduced intracellularly and incorporated within host cell DNA for expression, by homologous recombination (Koller and Smithies, 1989, Proc. Natl. Acad. Sci. USA 86:8932–8935; Zijlstra et al., 1989, Nature 342:435–438).

In a specific embodiment, a viral vector that contains the nucleic acid sequence encoding a chemokines, chemokine derivatives and/or chemokine analogs is used. For example, a retroviral vector can be used (see Miller et al., 1993, Meth. Enzymol. 217:581–599). These retroviral vectors have been modified to delete retroviral sequences that are not necessary for packaging of the viral genome. Retroviral vectors are maintained in infected cells by integration into genomic sites upon cell division. The nucleic acid to be used in gene therapy is cloned into the vector, which facilitates delivery of the gene into a patient. More detail about retroviral vectors can be found in Boesen et al., 1994, Biotherapy 6:291–302, which describes the use of a retroviral vector to deliver the mdr 1 gene to hematopoietic stem cells in order to make the stem cells more resistant to chemotherapy. Other references illustrating the use of retroviral vectors in gene therapy are: Clowes et al., 1994, J. Clin. Invest. 93:644–651; Kiem et al., 1994, Blood 83:1467–1473; Salmons and Gunzberg, 1993, Human Gene Therapy 4:129–141; and Grossman and Wilson, 1993, Curr. Opin. in Genetics and Devel, 3:110–114.

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, 1993, Current Opinion in Genetics and Development 3:499–503 present a review of adenovirus-based gene therapy. Bout et al., 1994, Human Gene Therapy 5:3–10 demonstrated the use of adenovirus vectors to transfer genes to the respiratory epithelia of rhesus monkeys. Other instances of the use of adenoviruses in gene therapy can be found in Rosenfeld et al., 1991, Science 252:431–434; Rosenfeld et al., 1992, Cell 68:143–155; and Mastrangeli et al., 1993, J. Clin. Invest. 91:225–234.

Adeno-associated virus (AAV) has also been proposed for use in gene therapy (Walsh et al., 1993, Proc. Soc. Exp. Biol. Med. 204:289–300.) Herpes viruses are other viruses that can also be used.

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including, but not limited to, transfection, electroporation, microinjection, infection with a viral vector containing the nucleic acid sequences, cell fusion, chromosome-mediated gene transfer, microcell-mediated gene transfer, spheroplast fusion, etc. Numerous techniques are known in the art for the introduction of foreign genes into cells (see e.g., Loeffler and Behr, 1993, Meth. Enzymol. 217:599–618; Cohen et al., 1993, Meth. Enzymol. 217:618–644; Cline, 1985, Pharmac. Ther. 29:69–92) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a patient by various methods known in the art. In a preferred embodiment, recombinant blood cells (e.g., hematopoietic stem or progenitor cells) are administered intravenously. Additionally, epithelial cells can be injected, e.g., subcutaneously, or recombinant skin cells (e.g., keratinocytes) may be applied as a skin graft onto the patient. The amount of cells envisioned for use depends on the desired effect, patient state, etc., and can be determined by one skilled in the art.

In an embodiment wherein recombinant cells are used in gene therapy, a nucleic acid sequence coding for chemokine, or therapeutically or prophylactically effective derivative, or analog is introduced into the cells such that it is expressible by the cells or their progeny, and the recombinant cells are then administered in vivo for therapeutic effect. In a specific embodiment, stem or progenitor cells, preferably hematopoietic stem or progenitor cells, are used. Any stem and/or progenitor cells which can be isolated and maintained in vitro can potentially be used in accordance with this embodiment of the present invention.

7.5.2 Demonstration of Therapeutic Utility

The therapeutics of the invention are preferably tested in vitro, and then in vivo for the desired therapeutic or prophylactic activity and/or for toxicity, prior to use in humans. While any in vitro or in vivo assays known in the art may be utilized to test the efficacy of a therapeutic of the invention, it is preferred that such is determined by applying one or more of the in vitro assays described infra.

7.5.3 Prophylactic Uses

The therapeutics of the invention can be administered to prevent viral replication or infection. The prophylactic methods of the invention can be used not only to prevent viral infection, but also to prevent post-infection viral replication or further infection that precedes disease development. It is particularly envisioned that administration can follow shortly after an individual engages in behavior that may expose such individual to the viral agent or otherwise render the individual at high risk for developing an immunodeficiency virus infection. Administration of the compositions of the invention may be used as a prophylactic measure in previously uninfected individuals after acute exposure to an HIV virus. Examples of such prophylactic use of the therapeutic of the invention may include, but is not limited to, prevention of immunodeficiency virus transmission from mother to fetus or infant (e.g., at parturition or through breast milk) and other settings where the likelihood of HIV transmission exists, such as, for example, accidents in health care settings wherein workers are exposed to HIV-containing blood products. Such administration is indicated where the therapeutic is shown in assays, as described supra, to have utility for treatment or prevention of the transmission of one or more immunodeficiency virus strains, preferably HIV.

7.6 Therapeutic/Prophylactic Compositions and Methods of Administering

The invention provides methods of treatment and prevention by administration to a subject wherein such treatment or prevention is desired a therapeutically or prophylactically effective amount of a therapeutic of the invention. The subject is preferably an animal, including, but not limited to, animals such as monkeys, sheep, cows, pigs, horses, chickens, cats, dogs, etc., and is preferably a mammal. and most preferably human. The subject can be a fetus, child, or adult. In a preferred aspect, the therapeutic is substantially purified.

Formulations and methods of administration that can be employed when the therapeutic comprises a nucleic acid are described above; additional appropriate formulations and routes of administration can be selected from among those described hereinbelow.

Various delivery systems are known and can be used to administer a therapeutic of the invention, e.g., encapsulation in liposomes, microparticles, microcapsules, recombinant cells capable of expressing the therapeutic, receptor-mediated endocytosis (see, e.g., Wu and Wu, 1987, J. Biol. Chem. 262:4429–4432), construction of a therapeutic nucleic acid as part of a retroviral or other vector, etc. Methods of introduction include but are not limited to intradermal, intramuscular, intraperitoneal, intravenous, subcutaneous, intranasal, epidural, and oral routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the therapeutic compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compositions of the invention locally to the area in need of treatment; this may be achieved, for example and not by way of limitation, by topical application, by injection, by means of a catheter, by means of a suppository, or by means of an implant, said implant being of a porous, non-porous, or gelatinous material, including membranes, such as sialastic membranes, or fibers.

In another embodiment, the therapeutic can be delivered in a vesicle, in particular a liposome (see Langer, 1990 Science 249:1527–1533; Treat et al., 1989, in Liposomes in the Therapy of Infectious Disease and Cancer, Lopez-Berestein and Fidler (eds.), Liss, New York, pp. 353–365; Lopez-Berestein, ibid., pp. 317–327; see generally ibid.)

In yet another embodiment, the therapeutic can be delivered in a controlled release system. In one embodiment, a pump may be used (see Langer, 1990, Science 249:1527–1533; Sefton 1987, CRC Crit. Ref. Biomed. Eng. 14:201; Buchwald et al., 1980; Surgery 88:507; Saudek et al., 1989, N. Engl. J. Med. 321:574). In another embodiment, polymeric materials can be used (see Medical Applications of Controlled Release, 1974, Langer and Wise (eds.), CRC Pres., Boca Raton, Fla.; Controlled Drug Bioavailability, Drug Product Design and Performance, 1984, Smolen and Ball (eds.), Wiley, New York; Ranger and Peppas, 1983; J. Macromol. Sci. Rev. Macromol. Chem. 23:61; see also Levy et al., 1985, Science 228:190; During et al., 1989, Ann. Neurol. 25:351; Howard et al., 1989, J. Neurosurg. 71:105). In yet another embodiment, a controlled release system can be placed in proximity of the therapeutic target, thus requiring only a fraction of the systemic dose (see, e.g., Medical Applications of Controlled Release, 1984, Langer and Wise (eds.), CRC Pres., Boca Raton, Fla., vol. 2, pp. 115–138).

Other controlled release systems are discussed in the review by Langer (1990, Science 249:1527–1533).

In a specific embodiment where the therapeutic is a nucleic acid encoding a protein therapeutic, the nucleic acid can be administered by gene therapy methods as described supra.

The present invention also provides pharmaceutical compositions. Such compositions comprise a therapeutically effective amount of a therapeutic, and a therapeutically acceptable carrier. In a specific embodiment, the term "therapeutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Therapeutic Sciences" by E. W. Martin. Such compositions will contain a therapeutically effective amount of the therapeutic, preferably in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The therapeutics of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The amount of the therapeutic of the invention which will be effective in the treatment of a particular disorder or condition will depend on the nature of the disorder or condition, and can be determined by standard clinical techniques. In addition, in vivo and/or in vitro assays may optionally be employed to help predict optimal dosage ranges. The precise dose to be employed in the formulation will also depend on the route of administration, and the seriousness of the disease or disorder, and should be decided according to the judgment of the practitioner and each patient's circumstances. However, suitable dosage ranges for intravenous administration are generally about 1–1000 micrograms of active compound per kilogram body weight. Suitable dosage ranges for intranasal administration are generally about 0.01 pg/kg body weight to 1 mg/kg body weight. Effective doses may be extrapolated from dose-response curves derived from in vitro or animal model test systems.

Suppositories generally contain active ingredient in the range of 0.5% to 10% by weight; oral formulations preferably contain 10% to 95% active ingredient.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

8. EXAMPLES

The invention is illustrated by the following non-limiting examples.

8.1 Primary Macrophage/HIV-1$_{BaL}$ Cell Free Infectivity Assay for Chemokine Suppression The following assay is used to determine the ability of a chemokines, chemokine derivatives and/or 15 chemokine analogs to interfere with the infection or replication of HIV$_{BaL}$. Peripheral blood mononuclear cells (PBMC's) ($2 \times 10^6$) are added to triplicate assay wells of a 48 well culture plate and cultured in 10 ng/ml recombinant human GM-CSF to mature the monocytes into macrophages. After 48 hours the nonadherent cells are washed away and the adherent cells cultured in GM-CSF for an additional 96 hours resulting in mature macrophages. The wells are again washed and then infected with 50 TCID$_{50}$ of HIV-1$_{BaL}$ (available from the NIH AIDS Research and Reference Reagent Program) that has been propagated in primary macrophages in the presence of chemokines, chemokine derivatives and/or chemokine analogs in a total volume of 200 µl (GM-CSF is no longer present). Each chemokines, chemokine derivatives and/or chemokine analogs concentration is tested in triplicate wells. Throughout the course of the experiment, controls are maintained wherein the cell medium containing the virus does not contain the test chemokines, chemokine derivatives and/or chemokine analogs. After an overnight (18 hour) incubation each well is washed to remove virus and replenished with fresh medium containing the corresponding amount of chemokine derivative, or analog. After 48 hours in culture the cells are refed with 200 µl of fresh medium with the corresponding concentration of chemokines, chemokine derivatives and/or chemokine analogs. Infectivity is determined by commercial HIV-1 p24 antigen capture ELISA on culture well supernatants were collected 5–7 days post-infection (Coulter, Hialeah, Fla.).

Reduced levels of virus in test samples as indicated by reduced levels of p24 in the ELISA relative to the control indicates that the chemokine, derivative, or analog interferes with the infection or replication of HIV-1$_{BaL}$ in primary macrophage cells at the concentration tested. Preferably, the chemokine derivative or analog reduces levels of virus, as measured by, for example, p24, by ⊒ 50% relative to control assays carried out in the absence of test compound.

8.2 Primary CD4$^+$ PBMC/Primary HIV-1 Isolate Cell-Free Infectivity Assay for Chemokine Suppression The following assay is used to determine the ability of a chemokines, chemokine derivatives and/or chemokine analogs to interfere with the infection or replication of a primary HIV-1 isolate in primary CD4$^+$ cells. Target cells can either be peripheral blood mononuclear cells (PBMC's) depleted of CD8$^+$ cells using anti-CD8 immunomagnetic beads or CD4$^+$ PBMC's purified with anti-CD4 immunomagnetic beads. Immunomagnetic bead depletion/purification protocols are carried out according to manufacturer's instructions (Dynal A.S., Norway).

Viruses are isolated according to procedures known in the art. Briefly, isolates are obtained by co-culturing of 1 to $2 \times 10^6$ PBMC's from HIV-1 infected individuals with phytohemagglutinin (PHA)-stimulated PBMC from two HIV-1 negative blood donors. The cultures are maintained in complete RPMI 1640 medium (Gibco) containing 10% fetal calf serum (FCS), 5U/ml of rIL2 (R & D Systems, Minneapolis, Minn.), 2 µg/ml polybrene (Sigma, St. Louis, Mo.) and antibiotics. Virus antigen production is measured in supernatants twice weekly using an HIV-1 p24 antigen capture ELISA (Coulter, Hialeah, Fla.). Virus stocks are generated from the p24 antigen capture assay positive supernatants by passaging of the virus isolates once or twice in PHA stimulated blood donor PBMC's. The virus containing supernatants are aliquotted and cryopreserved at −75EC.

The primary isolates are titered before use so that known doses can be assayed. To determine the 50% tissue culture infectious dose ($TCID_{50}$) of virus stocks, the PBMC's from one donor are activated with PHA and cultured for three days in complete medium of RPMI. The activated PBMC's are thereafter aliquotted in fetal calf serum containing 10% DMSO and cryopreserved at −15EC until use. At the time of virus stock titration and/or chemokine inhibition experiments, the activated PBMC's are thawed and expanded for 2–3 days in complete RPMI 1640 medium. As described in the protocol provided by the manufacturer (Dynal A.S., Norway), $CD8^+$ T cells are depleted from the activated PBMC's using Dynabeads M-450 CD8. $CD8^+$ T-cell depleted PBMC's at a concentration of $1\times10^5$ cells per well in complete medium are seeded in each well in microtiter plates (96 wells, Nunc, Denmark). Virus stocks are thawed and serially diluted in five fold steps starting from a dilution of 1:2. Each dilution of virus inoculum prepared in complete medium is added to the seeded cell suspension in equal volumes following incubation at 37EC. After one hour incubation, complete RPMI 1640 is added to each well so that total volume per one well is 250 μl. The old medium is removed and new complete medium is added at day three post infection. The harvested culture medium is evaluated for HIV-1 p24 at day seven. The $TCID_{50}$ value is defined as the reciprocal of the virus dilution resulting in 50% positive wells using Reed-Muench calculation or the Spearman-Karber equation.

Phytohemagglutinin (PHA)-activated target cells ($2\times10^5$) are incubated for 1–2 hours with 10–50 $TCID_{50}$ of a primary isolate of non-syncytium inducing (NSI) or syncytium-inducing (SI) HIV-1 (which has been obtained from a patient as described above and propagated only in primary PBMC's) in the presence of chemokines, derivatives or analogs in a total volume of 200–1000 μl.

Controls consist of wells containing the cells, primary HIV-1 isolate, and culture medium in place of chemokine derivative or analog. The cells are then washed to remove virus and replenished with fresh medium containing the corresponding amount of chemokine. After 48 hours in culture the cells are refed with 200 μl of fresh medium with the corresponding concentration of chemokine. Infectivity is determined by HIV-1 p24 antigen capture ELISA of culture well supernatants were collected 5–7 days post-infection (Coulter, Hialeah, Fla.).

Reduced levels of virus in test samples as indicated by reduced levels of p24 in the ELISA relative to the controls indicate that the chemokines, chemokine derivatives and/or chemokine analogs interferes with the infection of the primary HIV isolate in primary $CD4^+$ cells.

8.3 PM1/HIV-$1_{BaL}$ Cell-Free Infectivity Assay for Chemokine Suppression

The following assay is used to determine the ability of a chemokines, chemokine derivatives and/or chemokine analogs to interfere with the infection or replication of HIV-$1_{BaL}$ in the $CD4^+$ T-cell clone (PM1) which is susceptible to both primary and macrophage-tropic HIV-1 isolates. The PM1/HIV-$1_{BaL}$ test system is standardized in 48-well microliter plates using PM1 cells (available from the NIH AIDS Research and Reference Reagent Program) acutely infected with HIV-$1_{BaL}$. PM1 cells ($2\times10^5$/test) are infected with HIV-$1_{BaL}$ (10–50 $TCID_{50}$/$1\times10^6$ cells) for 2 hr at 37EC, then washed three times with pre-warmed phosphate buffered saline (PBS) and resuspended in complete culture medium (250 μl per test) containing different dilutions of the chemokine, derivative and/or analog composition to be assayed. At least four untreated controls, resuspended in complete medium, with or without exogenous interleukin-2 (IL-2), are always handled in parallel to treated cultures. The controls do not contain the chemokines, chemokine derivatives and/or chemokine analogs. At day 3 post-infection, 250 μl of fresh chemokines, chemokine derivatives and/or chemokine analogs composition containing the same original concentration of the respective test composition is added to each culture. The level of virus replication is assessed by measuring the release of extracellular p24 core antigen at different days postinfection. Five to nine days postinfection, the cultures are harvested, centrifuged to remove the cells and tested for HIV-1 p24 antigen by a commercial ELISA test (Coulter, Hialeah, Fla.).

Reduced levels of virus in test samples as indicated by reduced levels of p24 in the ELISA relative to the controls indicate that the chemokine, derivative, or analog interferes with HIV$_{BaL}$ infection of in PM1 cells at the concentration tested. Preferably, the chemokine derivative or analog reduces levels of virus, as measured by, for example, p24, by ∃ 50% relative to control assays carried out in the absence of test compound.

8.4 Assay of HIV$^+$ PBMCS for Suppression of HIV in the Presence of Chemokines The following assay is used to determine the ability of a chemokines, chemokine derivatives and/or chemokine analogs to interfere with the ability of a primary HIV-1 isolate from HIV peripheral blood mononuclear cells to replicate and/or infect other $CD4^+$ cells.

$CD4^+$ T cells ($1\times10^5$) from uninfected individuals (purified with anti-CD4 immunomagnetic beads) or CD8-depleted PBMC's (cells removed by anti-CD8 immunomagnetic beads) are incubated with ∃ 1000 $CD4^+$ peripheral blood cells from the infected individual in the presence of different concentrations e.g., 1 ng/ml to 1 μg/ml of test chemokines, chemokine derivatives and/or chemokine analogs in culture wells. Controls consist of $CD4^+$ infected and non-infected incubations wherein chemokine has not been added. For many individuals with advanced infection, $CD4^+$ T cell levels are very low. In these cases, as many cells as possible are incubated with the uninfected $CD4^+$ target cells. The test chemokine concentration is maintained throughout the duration of culture. Culture supernatant samples are removed periodically (every 2–3 days) and tested for virus expression by commercial HIV-1 p24 antigen capture ELISA. Virus is usually detected by day 7.

Reduced levels of virus in the test sample relative to the $CD4^+$ infected controls as indicated by reduced levels of p24 in the ELISA indicate that the chemokines, chemokine derivatives and/or chemokine analogs interferes with infection or replication of the HIV$^+$ peripheral blood cell HIV-1 isolate in $CD4^+$ cells. Preferably, the chemokine derivative or analog reduces levels of virus, as measured by, for example, p24, by ∃ 50% relative to control assays carried out in the absence of test compound.

8.5 Assay for the Effect of Compositions of the Invention on Cellular Proliferation and Viability To rule out the possibility that the antiviral activity of the compositions assayed as described above may be due to a negative effect on cellular viability or proliferation, the effect of these compositions on the proliferative response and viability of the target cells is determined for every in vitro test. For example, the effect of the chemokine, derivative, or analog tested in the primary $CD4^+$ PBMC/primary HIV-$1_{BaL}$ isolate cell-free infectivity assay on the proliferative response of primary $CD4^+$ PBMC may be determined. Peripheral blood mononuclear cells are separated by Ficoll gradient centrifugation and placed in round-bottom 96-well plates ($10^5$ cells/well). [$^3$H]-Thymidine incorporation by stimulated cells is monitored in the presence of concentrations of the compositions corresponding to that used in the in vitro suppression assay and compared with [$^3$H]-Thymidine incorporation in controls that have not been treated with the test composition. The test sample average corrected counts per minute from triplicate cultures and the percent radionucleotide incorporation is compared with that observed for the control. Comparable levels of [$^3$H]-Thymidine incorporation in the test and control samples is indicative that antiviral activity observed in the cell free infectivity assay is not due to the suppression of cellular proliferation.

The effect of the chemokine, derivative, or analog tested on the viability of primary CD4$^+$ PBMC is determined applying techniques known in the art using trypan blue dye exclusion.

8.6 Mixture of MDC with I-309 is Especially Potent and Titratable

HIV IIIB was mixed with PBMC at a multiplicity of infection of 0.001–0.0025 and incubated for 2 hours at 37° C. in RPMI 1640 medium containing 10% fetal calf serum (complete medium). The cells were then washed and placed in microtiter culture wells with the indicated amounts of chemokines in complete medium. Cells were then cultured in a $CO_2$ incubator at 37° C. Culture supernatants were collected 4 days post-infection and tested for infection by HIV p24 capture ELISA.

For the antibody experiments, (FIGS. 2–4) primary CD8$^+$ T cells from a series of HIV-seronegative donors were activated by PHA and 10 ng/ml IL-2 in complete medium for 3 days. The cells were then washed and cultured in complete medium with 10 ng/ml IL-2 in a $CO_2$ incubator. Eight days post-activation, culture supernatants were collected. A portion of each supernatant was tested directly for HIV-inhibiting activity in the infectivity assay above. Another portion was treated with the indicated concentrations of neutralizing anti-chemokine antibodies and tested in parallel, If the chemokines contribute to the inhibitory activity in the supernatants, treatment with the antibodies should restore infection.

FIG. 1 demonstrates how mixtures of chemokines at the low concentrations released by primary activated CD8+ T cells (as determined by ELISA) block both R5 and X4 HIV infection. The mixture of MDC with I-309 is especially potent and titratable. The figure also shows that even at much higher concentrations, either I-309 or MDC alone have much less antiviral effect, so they must cooperate or synergize to mediate potent antiviral activity in the mix. Also presented for comparison are tests (right panel) with four randomly selected supernatants from activated CD8+ T cells. Two test dilutions are shown. The "50%" sups contain the levels of the chemokines used in the mix. As is apparent, the mix is as potent as the supernatants; therefore the mix recapitulates the natural antiviral activity produced by primary cells.

Figure 2:
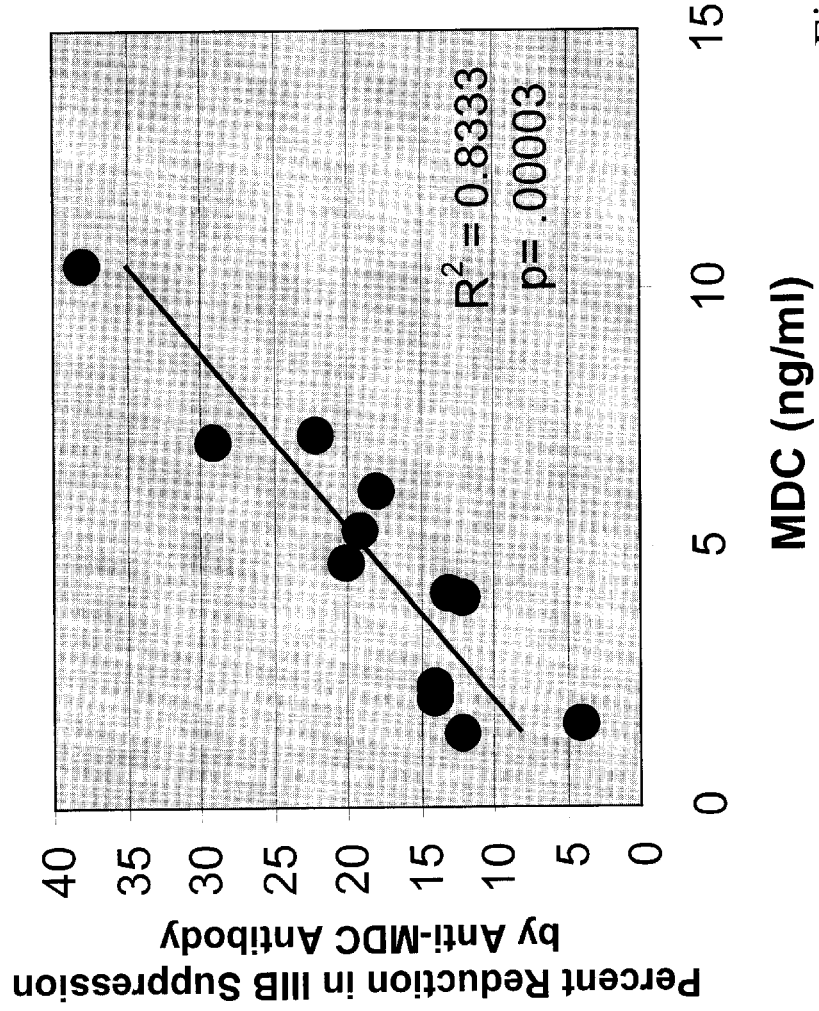
FIG. 2 shows the contribution of MDC to soluble $HIV_{IIIB}$ suppressive activity produced by primary CD8+ T cells. The figure demonstrates that the more MDC the cells make, the more it contributes to the antiviral effect.
Figure 3:
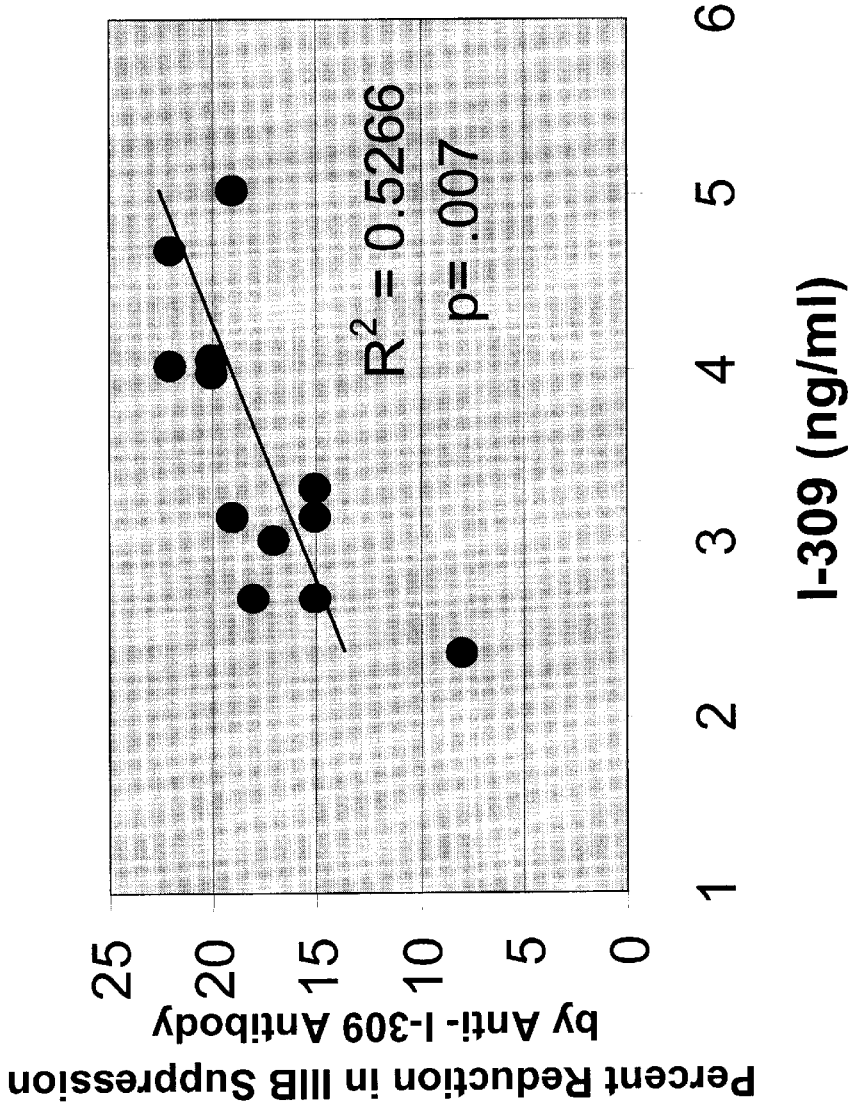
FIG. 3 shows the same form of analyses on I-309, using an anti-I-309 antibody.

FIG. 2 shows the contribution of MDC to soluble HIV$_{IIIB}$ suppressive activity produced by primary CD8+ T cells. Supernatants from the cells that block HIV were treated with an antibody that blocks MDC activity. The reduction in antiviral activity was then plotted versus the amount of MDC present (as determined by ELISA) in the same supernatant that was treated. The figure demonstrates that the more MDC the cells make, the more it contributes to the antiviral effect. FIG. 3 shows the same form of analysis on I-309, using an anti-I-309 antibody. FIG. 4 shows the same analyses using a mixture of antibodies to I-309 and MDC. This figure shows that the two chemokines contribute very significantly to the natural activity produced by primary CD8+ T cells.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

Various references are cited herein, the disclosures of which are incorporated by reference in their entireties.

What is claimed is:

1. A method of formulating a composition comprising one or more chemokines for use in a pharmaceutical composition having anti-HIV activity against one or more HIV-1 isolates present in an individual at a given time, the method comprising:

(a) contacting a first aliquot of HIV$^+$ cells obtained from said individual with a chemokine compound, wherein the chemokine compound comprises a member selected from the group consisting of:
  (i) at least one chemokine selected from the group consisting of MDC, MCP-1, MCP-2, MCP-3, MCP-4, MIP-1γ, MIP-3α, MIP-3β, eotaxin, Exodus, I-309, γIP-10, PF4, NAP-2, GRO-α, GRO-β, GRO-γ, ENA-78, GCP-2, and lymphotactin; and
  (ii) at least one chemokine of (i) comprising one or more conservative substitution, terminal additions and/or terminal deletions; and
 (b) comparing the ability to isolate HIV from said cells with the ability to isolate HIV from a second aliquot of HIV$^+$ cells obtained from said individual that are not contacted with said chemokine compound
 (c) formulating the composition to comprise the chemokine compound which produces a decrease in the ability to isolate virus in the presence of said chemokine compound in the HIV$^+$ cells of the individual.

2. The method of claim 1, further comprising the step of combining in the composition two or more of said chemokines, demonstrating anti-viral activity against said HIV-1 isolates.

3. The method of claim 2 wherein at least 3 of said chemokines are combined.

4. The method of claim 1 further comprising repeating said contacting and comparing steps for at least 2 individual chemokines.

5. The method of claim 1 further comprising repeating said contacting and comparing steps for at least 3 individual chemokines.

6. The method of claim 1 wherein the HIV$^+$ cells are co-cultured with uninfected CD4$^+$ peripheral blood mononuclear cells prior to said contacting with the chemokines.

7. A method of formulating a pharmaceutical composition for a particular subject infected with HIV, the method comprising:

assaying at least one chemokine for the ability to inhibit:
  HIV infection;
  HIV replication; or
  expression of an RNA or protein of HIV;
  wherein said HIV is a primary isolate recovered from said subject; and
 combining an amount effective of one or more of said chemokines demonstrating said ability with a pharmaceutically acceptable carrier to decrease the viral load in the isolate of said subject.

8. The method of claim 7 wherein said assaying of the chemokine is by a method comprising:

measuring HIV-1 levels in primary macrophage cells or primary CD4$^+$ peripheral blood mononuclear cells incubated with the primary isolate, which cells have been contacted with the chemokine; and comparing the measured HIV-1 levels in the cells which have been contacted with the chemokine with said levels in cells not so contacted with the chemokine, wherein a lower level in said contacted cells indicates that the chemokine has anti-HIV activity.

9. The method of claim 8 wherein primary CD4$^+$ peripheral blood mononuclear cells are incubated with the primary isolate.

10. The method of claim 8 wherein the primary isolate has been propagated and maintained only in macrophages.

11. The method of claim 8 wherein the primary isolate is syncytia inducing.

12. The method of claim 8 wherein the primary isolate is non-syncytia inducing.

13. The method of claim 7 wherein said assaying of the chemokine is by a method comprising:

measuring HIV-1 levels in cultures of HIV$^+$ cells obtained from the subject which have been contacted with the chemokine; and comparing said measured HIV-1 levels with said levels in said cells not so contacted with the chemokine, wherein a lower HIV-1 level in cultures of said contacted cells indicates that the chemokine has anti-HIV activity.

14. The method of claim 13 further comprising repeating steps (a) and (b) for at least 2 individual chemokines.

15. The method of claim 7 wherein the chemokine is a chemokine derivative and/or chemokine analog.

16. The method of claim 14 or 15 wherein the chemokine is selected from the group consisting of MDC, MCP-1, MCP-2, MCP-3, MCP-4, MIP-1γ, MIP-3α, MIP-3β, eotaxin, Exodus, I-309, γIP-10, PF4, NAP-2, GRO-α, GRO-β, GRO-γ, ENA-78, GCP-2, and lymphotactin.

17. A method of inhibiting HIV infection or replication in cells of a subject in need of such treatment, the method comprising administering to the subject a pharmaceutical composition comprising:

at least one chemokine selected from the group consisting of MDC, MCP-1, MCP-2, MCP-3, MCP-4, MIP-1γ, MIP-3α, MIP-3β, eotaxin, Exodus, I-309, γIP-10, PF4, NAP-2, GRO-α, GRO-β, GRO-γ, ENA-78, GCP-2, and lymphotactin in an amount effective to inhibit HIV infection or replication in the cells of the subject; and a pharmaceutically acceptable carrier.

18. The method of claim 17 wherein the only chemokines in said composition are those demonstrated to have activity against a primary HIV isolate from said subject.

19. The method of claim 17 wherein said pharmaceutical composition comprises at least 2 of said chemokines.

20. A method of decreasing a HIV viral load in a subject in need of such treatment, the method comprising administering to the subject a pharmaceutical composition comprising:

at least one nucleic acid encoding a chemokine selected from the group consisting of MDC, MCP-1, MCP-2, MCP-3, MCP-4, MIP-1γ, MIP-3α, MIP-3β, eotaxin, Exodus, I-309, γIP-10, PF4, NAP-2, GRO-α, GRO-β, GRO-γ, ENA-78, GCP-2, and lymphotactin, in an amount effective to decrease the HIV viral load; and a pharmaceutically acceptable carrier.

21. The method of claim 20 wherein said composition comprises nucleic acids encoding at least 2 of said chemokines.

22. The method of claim 20 further comprising administering to the subject an anti-viral drug other than a chemokine, in an amount effective to inhibit HIV infection or replication.

23. The method of claim 22 wherein the other anti-viral drug is selected from one or more of the group consisting of AZT, ddI, ddC, 3TC, and sequinavir.

24. The method of claim 22 wherein the protein is administered intramuscularly.

25. A method of inhibiting HIV infection or replication in a subject in need of such treatment, the method comprising administering to the subject a composition comprising:

a first nucleic acid encoding RANTES, MIP-1α, MIP-1β, or IL-8, and a second nucleic acid encoding a chemokine selected from the group consisting of MCP-1, MCP-2, MCP-3, MCP-4, MIP-1γ, MIP-3α, MIP-362, eotaxin, Exodus, I-309, γIP-10, PF4, NAP-2, GRO-α, GRO-β, GRO-γ, ENA-78, GCP-2, lymphotactin and SDF-1;

together in an amount effective to inhibit HIV infection or replication.

26. A pharmaceutical composition comprising:

at least one chemokine selected from the group consisting of MDC, MCP-2, MCP-4, MIP-1γ, MIP-3α, MIP-3β, eotaxin, Exodus, I-309, γIP-10, PF4, NAP-2, GRO-α, GRO-β, GRO-γ, ENA-78, GCP-2, and lymphotactin, in an amount effective to decrease a HIV viral load in infected cells; and a pharmaceutically acceptable carrier.

27. The pharmaceutical composition of claim 26 wherein the chemokine is purified.

28. The pharmaceutical composition of claim 26 further comprising at least 1, 2, 3, 4, 5, 6, 8, or 9 chemokines in an amount effective to inhibit HIV infection or replication.

29. The pharmaceutical composition of claim 26 further comprising at least one member selected from the group consisting of RANTES, MIP-1α, MIP-1β, MCP-1, MCP-3, IL-8 or SDF-1 together in an amount effective to inhibit HIV infection or replication.

30. The pharmaceutical composition of claim 29 wherein the chemokine is a chemokine derivative and/or chemokine analog.

31. A pharmaceutical composition comprising:

two or more chemokines, each of which binds to at least one chemokine receptor selected from the group consisting of CC CKR-1, CC CKR-2A, CC CKR-2B, CC CKR-3, CC CKR-4, CC CKR-5, CxC CKR4, IL-8RA, IL-8RB, Mig receptor, γIP-10 receptor and Duffy antigen, in an amount effective to inhibit HIV infection or replication in infected cells; and a pharmaceutically acceptable carrier.

32. A method of formulating a pharmaceutical composition having anti-HIV activity against one or more HIV-1 isolates present in an individual at a given time, the method comprising:

contacting a first aliquot of CD4$^+$ cells, one or more virus isolates obtained from said individual, and a chemokine; and comparing the ability to isolate HIV from said cells with the ability to isolate HIV from a second aliquot of CD4$^+$ cells contacted with said virus isolates that are not contacted with said chemokines, wherein a decrease in the ability to isolate virus in the presence of said chemokines is indicative that the chemokines has anti-viral activity against said HIV-1 isolates.

33. A pharmaceutical composition comprising MDC and I-309 in an effective amount to exhibit anti-HIV activity in human cells; and a pharmaceutically acceptable carrier.

34. The method of claim 17 wherein the MDC and I-309 are administered in a synergistically effective and therapeutically effective amount.

* * * * *

UNITED STATES PATENT AND TRADEMARK OFFICE
CERTIFICATE OF CORRECTION

PATENT NO. : 6,428,970 B2
APPLICATION NO. : 09/747142
DATED : August 6, 2002
INVENTOR(S) : Anthony De Vico et al.

It is certified that error appears in the above-identified patent and that said Letters Patent is hereby corrected as shown below:

| | |
|---|---|
| Column 4, line 49: | "CD8⁻" should be -- $CD8^+$ -- |
| Column 5, line 58: | "inhabiting" should be -- inhibiting -- |
| Column 6, line 41: | "an a chemokine" should be -- an á chemokine -- |
| Column 7, line 33: | "analogs. and/or" should be -- analogs and/or -- |
| Column 9, line 39: | "chemokincs" should be -- chemokines -- |
| Column 14, lines 1-2: | "an a chemokine" should be -- an á chemokine -- |
| Column 14, line 2: | "to. CxC" should be -- to, CxC -- |
| Column 15, line 51: | "PVP. 0.1%" should be -- PVP, 0.1% -- |
| Column 18, line 28: | "arc" should be -- are -- |
| Column 18, line 30: | "embodiments. the" should be -- embodiments, the -- |
| Column 20, line 40: | "et at." should be -- et al. -- |
| Column 21, line 21: | "In addition. a" should be -- In addition, a -- |
| Column 27, line 21: | "CD4" should be -- $CD4^+$ -- |
| Column 35, line 24: | "mammal. and" should be -- mammal, and -- |
| Column 37, line 67: | "and/or 15 chemokine" should be -- and/or chemokine-- |

UNITED STATES PATENT AND TRADEMARK OFFICE
CERTIFICATE OF CORRECTION

PATENT NO. : 6,428,970 B2
APPLICATION NO. : 09/747142
DATED : August 6, 2002
INVENTOR(S) : Anthony De Vico et al.

It is certified that error appears in the above-identified patent and that said Letters Patent is hereby corrected as shown below:

Column 44, line 10: "MIP-362" should be -- MIP-3â --

Signed and Sealed this

Twenty-second Day of January, 2008

JON W. DUDAS
*Director of the United States Patent and Trademark Office*